United States Patent
Power

(10) Patent No.: US 11,857,741 B2
(45) Date of Patent: Jan. 2, 2024

(54) LOOPED WIRE FOR ADVANCED STENT GRAFTS AND METHODS OF USING SAME

(71) Applicant: W. L. Gore & Associates, Inc., Newark, DE (US)

(72) Inventor: Adam Power, London (CA)

(73) Assignee: W. L. Gore & Associates, Inc., Newark, DE (US)

(*) Notice: Subject to any disclaimer, the term of this patent is extended or adjusted under 35 U.S.C. 154(b) by 1048 days.

(21) Appl. No.: 16/489,820

(22) PCT Filed: Feb. 28, 2018

(86) PCT No.: PCT/CA2018/050229
§ 371 (c)(1),
(2) Date: Aug. 29, 2019

(87) PCT Pub. No.: WO2018/157243
PCT Pub. Date: Sep. 7, 2018

(65) Prior Publication Data
US 2020/0008926 A1   Jan. 9, 2020

Related U.S. Application Data

(60) Provisional application No. 62/465,340, filed on Mar. 1, 2017.

(51) Int. Cl.
*A61M 25/09*   (2006.01)
*A61F 2/954*   (2013.01)
(Continued)

(52) U.S. Cl.
CPC .............. *A61M 25/09* (2013.01); *A61F 2/95* (2013.01); *A61F 2/954* (2013.01); *A61F 2/07* (2013.01);
(Continued)

(58) Field of Classification Search
CPC ......... A61M 25/09; A61M 2025/09175; A61F 2/95; A61F 2/954; A61F 2/07; A61F 2002/065; A61F 2002/067; A61B 5/6851
See application file for complete search history.

(56) References Cited

U.S. PATENT DOCUMENTS

| | | | |
|---|---|---|---|
| 6,517,550 B1 * | 2/2003 | Konya | A61B 17/221 606/113 |
| 2003/0004560 A1 | 1/2003 | Chobotov et al. | |

(Continued)

FOREIGN PATENT DOCUMENTS

| | | |
|---|---|---|
| AU | 2021224755 A1 | 8/2022 |
| EP | 1793886 B1 | 11/2008 |

(Continued)

OTHER PUBLICATIONS

Canadian Intellectual Property Office, International Search Report and Written Opinion against PCT/CA2018/050229, dated May 28, 2018, 12 pages.

*Primary Examiner* — Timothy J Neal
*Assistant Examiner* — Andrew P. Restaino

(57) ABSTRACT

A looped wire is provided for placing an endograft into a blood vessel. The looped wire comprising a flexible guidewire with one or more loops distributed along its length. The one or more loops have an inner diameter that is larger than the thickness of a suture or wire for threading the suture or wire through. The one or more loops is adapted for sliding along the suture or wire. Endograft system comprising the looped wire, and methods of using the looped wire are also provided.

25 Claims, 18 Drawing Sheets

(51) Int. Cl.
*A61F 2/95* (2013.01)
*A61F 2/07* (2013.01)
*A61F 2/06* (2013.01)

(52) U.S. Cl.
CPC .................. *A61F 2002/065* (2013.01); *A61M 2025/0915* (2013.01); *A61M 2025/09108* (2013.01); *A61M 2025/09133* (2013.01); *A61M 2025/09141* (2013.01); *A61M 2025/09175* (2013.01)

(56) References Cited

U.S. PATENT DOCUMENTS

| | | | |
|---|---|---|---|
| 2005/0182476 A1 | 8/2005 | Hartley et al. | |
| 2008/0172122 A1 | 7/2008 | Mayberry et al. | |
| 2008/0208309 A1* | 8/2008 | Saeed | A61F 2/954 |
| | | | 623/1.11 |
| 2008/0255656 A1* | 10/2008 | Saeed | A61F 2/954 |
| | | | 623/1.12 |
| 2011/0130828 A1* | 6/2011 | Sithian | A61F 2/07 |
| | | | 623/1.23 |
| 2012/0184982 A1 | 7/2012 | Hierbowy et al. | |
| 2013/0103131 A1* | 4/2013 | Goetz | A61F 2/2439 |
| | | | 623/1.11 |
| 2015/0250481 A1 | 9/2015 | Chobotov | |
| 2016/0158043 A1 | 6/2016 | Ehnes et al. | |
| 2019/0231514 A1 | 8/2019 | Arbefeuille | |
| 2021/0212699 A1 | 7/2021 | Herbowy et al. | |
| 2022/0192851 A1 | 6/2022 | Garcia | |
| 2023/0125012 A1 | 4/2023 | Kerr et al. | |

FOREIGN PATENT DOCUMENTS

| | | |
|---|---|---|
| EP | 1377234 B1 | 1/2013 |
| EP | 2665422 A1 | 11/2013 |
| EP | 0000001 A1 | 6/2016 |
| EP | 2749251 B1 | 7/2016 |
| EP | 3091944 A1 | 11/2016 |
| EP | 2117631 B1 | 7/2017 |
| EP | 3116439 B1 | 2/2018 |
| EP | 2985007 B1 | 11/2019 |
| EP | 3028681 B1 | 12/2019 |
| EP | 3585306 B1 | 1/2021 |
| EP | 3932373 A1 | 1/2022 |
| EP | 3585320 B1 | 7/2022 |
| WO | 200024449 A1 | 5/2000 |
| WO | 2004050161 A1 | 6/2004 |
| WO | 2006/039217 A1 | 4/2006 |
| WO | 2006039216 A2 | 4/2006 |
| WO | 2007/011510 A2 | 1/2007 |
| WO | 2007/035895 A2 | 3/2007 |
| WO | 2008030737 A2 | 3/2008 |
| WO | 2008/089097 A1 | 7/2008 |
| WO | 2012/148715 A2 | 11/2012 |
| WO | 2014/066104 A1 | 5/2014 |
| WO | 2015/023880 A1 | 2/2015 |
| WO | 2015/105530 A1 | 7/2015 |
| WO | 2018/156847 A1 | 8/2018 |
| WO | 2018/156852 A1 | 8/2018 |
| WO | 2018/156853 A1 | 8/2018 |

\* cited by examiner

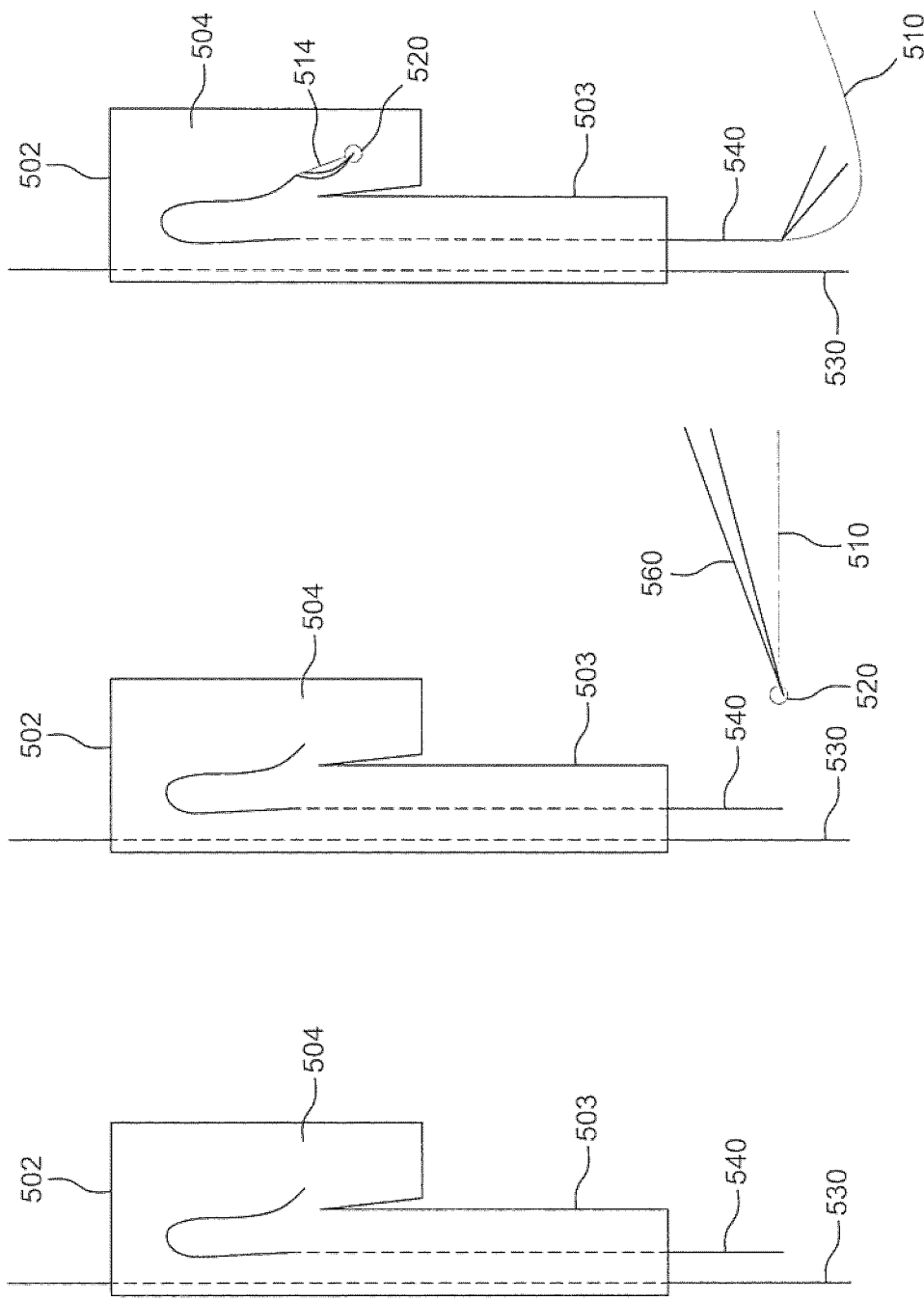

LOOPED WIRE FOR ADVANCED STENT GRAFTS AND METHODS OF USING SAME

RELATED APPLICATIONS

The present application claims priority from U.S. Provisional Application No. 62/465,340, the contents of which are incorporated herein by reference in its entirety.

FIELD

The present disclosure relates to wires and devices for assisting in the repair of aneurysms by endovascular means.

BACKGROUND

Endovascular aneurysm repair (EVAR) or thoracic endovascular aneurysm repair (TEVAR) can be challenging and time-consuming procedures for the treatment of aortic aneurysms. These types of procedures are particularly difficult when the aneurysms involve blood vessels such as the renal arteries or visceral arteries which branch off from the abdominal aorta to supply blood to various organs. Other blood vessels with branches that can be involved in aortic aneurysms include the aortic arch which has three branches (and anatomical variations thereof), or the common iliac arteries which are two large arteries originating from the aortic bifurcation that branch into the external and internal iliac arteries.

To accommodate branch blood vessels involved in aneurysms, specialized endografts called fenestrated or branched endografts are often used. Major branch arteries to various crucial body parts or organs may originate from the aneurysm, in which case an endovascular repair must also preserve blood flow to these critical arteries. A fenestrated endograft has holes (fenestrations) in the graft body to maintain the patency of the branched blood vessels. Procedures using a fenestrated endografts are called fenestrated endovascular aortic/aneurysm repair (FEVAR). A branched endograft (BEVAR) involves small branches in the graft body instead of fenestrations for the branch blood vessels. Both FEVAR and BEVAR usually involve deployment of bridging stents from the main body into each major branch artery. These fenestrations or branches provide portals where balloon-expandable as well as self-expanding covered stents (ie. bridging stents) can be deployed to bridge into target vessels. However, all of these procedures are long, technically difficult, and currently only performed in a few centers.

SUMMARY

Given the time-consuming and technically challenging nature of FEVAR and BEVAR procedures, there exists a need for improved procedures as well as tools that allow these procedures to be performed more efficiently.

In at least one aspect there is provided a looped wire for placing an endograft into a blood vessel, the looped wire comprising a flexible guidewire having a leading end and a lagging end, and one or more loops distributed along the length of the guidewire; wherein the one or more loops have an inner diameter that is larger than the thickness of a strand of material for threading the strand of material through the one or more loops and for sliding engagement with the strand of material.

In one embodiment there is provided the looped wire described herein, wherein the strand of material is a suture or a thread, and the looped wire is adapted for snaring an endovascular wire.

In one embodiment there is provided the looped wire described herein, wherein the strand of material is an endovascular wire, and the one or more loops have an inner diameter that is about 0.002 to 0.003 inches larger than the diameter of the endovascular wire, for sliding the one or more loops along the length of the endovascular wire by passing a catheter or sheath over the endovascular wire.

In one embodiment there is provided the looped wire described herein, wherein the one or more loops have an inner diameter of about 0.038 inches for threading a 0.035 inch endovascular wire through the one or more loops.

In one embodiment there is provided the looped wire described herein, wherein the one or more loops have an inner diameter of about 0.040 inches for threading a 0.038 inch endovascular wire through the one or more loops.

In one embodiment there is provided the looped wire described herein, wherein the guidewire is 0.018 inch in diameter.

In one embodiment there is provided the looped wire described herein, wherein the guidewire is made of nitinol.

In one embodiment there is provided the looped wire described herein, wherein the guidewire is a PTFE coated nitinol wire.

In one embodiment there is provided the looped wire described herein, wherein the one or more loops are compressible into a compressed state for advancing the looped wire through a catheter.

In one embodiment there is provided the looped wire described herein, wherein in the compressed state the one or more loops have a width of less than 0.035 inches for insertion through a 0.035 inch catheter.

In one embodiment there is provided the looped wire described herein, wherein the leading end of the guidewire comprises a first floppy tip.

In one embodiment there is provided the looped wire described herein, wherein the lagging end of the guidewire comprises a second floppy tip.

In one embodiment there is provided the looped wire described herein, wherein the first and/or the second floppy tip comprises a tapered portion of the guidewire.

In one embodiment there is provided the looped wire described herein, wherein the first and/or the second floppy tip is made by heating the leading and/or lagging end.

In one embodiment there is provided the looped wire described herein, wherein the one or more loops are open loops, each having a fastening means for opening and closing the loops.

In one embodiment there is provided the looped wire described herein, wherein the one or more loops are detachable.

In one embodiment there is provided the looped wire described herein, comprising a first loop located proximate to the leading end of the guidewire.

In one embodiment there is provided the looped wire described herein, wherein the first loop is located at the leading end of the guidewire.

In one embodiment there is provided the looped wire described herein, further comprising a second loop located proximate to the lagging end of the guidewire.

In one embodiment there is provided the looped wire described herein, wherein the second loop is located at the lagging end of the guidewire.

In one embodiment there is provided the looped wire described herein, wherein the first loop is formed by looping the leading end of the guidewire.

In one embodiment there is provided the looped wire described herein, wherein the second loop is formed by looping the lagging end of the guidewire.

In one aspect there is provided a pre-cannulated endograft system comprising: an endograft; a primary endovascular wire extending through a main body stent of the endograft; and one or more pre-cannulation wires comprising the looped wire; wherein the primary endovascular wire is threaded through each of the first loops in sliding engagement at a point ahead of the endograft, for anchoring the one or more pre-cannulation wires to the primary endovascular wire.

In one embodiment there is provided the pre-cannulated endograft system described herein, wherein the endograft comprises one or more fenestrations or branches, and wherein the one or more pre-cannulation wires extend through the main body stent and out through the one or more fenestrations or branches.

In one embodiment there is provided the pre-cannulated endograft system described herein, wherein the endograft comprises a plurality of fenestrations or branches, wherein the endograft system comprises at least the same number of pre-cannulation wires as there are fenestrations or branches; and wherein each of the plurality of fenestrations or branches has at least one pre-cannulation wire extending there through.

In one embodiment there is provided the pre-cannulated endograft system described herein, wherein the primary endovascular wire are threaded through the first loops of the pre-cannulation wires based on order of use.

In one embodiment there is provided the pre-cannulated endograft system described herein, wherein each of the one or more pre-cannulation wires has a second loop located proximate to the lagging end of the guidewire.

In one embodiment there is provided the pre-cannulated endograft system described herein, wherein the endograft is a thoracoabdominal branch endoprothesis or an iliac branch graft.

In at least one aspect there is provided a method of placing an endograft in a target blood vessel for the treatment of an aneurysm, the method comprising sliding the first loop of the looped wire along the length of a primary endovascular wire to advance the looped wire through a blood vessel, wherein the first loop is threaded with the primary endovascular wire.

In one embodiment there is provided the method described herein comprising removing the looped wire from the primary endovascular wire by sliding the first loop off a free end of the endovascular wire.

In one embodiment there is provided the method described herein comprising advancing the primary endovascular wire and the looped wire into the blood vessel, through a first access point.

In one embodiment there is provided the method described herein wherein sliding the first loop along the length of the primary endovascular wire comprises advancing a pre-cannulated endograft system over the primary endovascular wire through the blood vessel, wherein the pre-cannulated endograft system comprises one or more stents and/or fenestrations and the looped wire extends through one of the one or more stents and/or fenestrations.

In one embodiment there is provided the method described herein further comprising: passing a catheter over the looped wire from the leading or lagging end; removing the looped wire from the catheter; and inserting a secondary endovascular wire through the catheter to a target location, for advancing a stent over the secondary endovascular wire to the target location.

In one embodiment there is provided the method described herein further comprising advancing a stent over the looped wire to a target location.

In one embodiment there is provided the method described herein, wherein the looped wire comprises a second loop located proximate the lagging end, and further comprising: threading a tertiary endovascular wire through the second loop, for anchoring the lagging end of the looped wire to the tertiary endovascular wire; advancing the tertiary endovascular wire and the lagging end of the looped wire into the blood vessel through the first access point; and sliding the second loop along the length of the tertiary endovascular wire to a target location.

In one embodiment there is provided the method described herein, wherein sliding the second loop comprises passing a catheter or sheath over the tertiary endovascular wire to push the second loop along the length of the tertiary endovascular wire to the target location.

In one embodiment there is provided the method described herein, further comprising: advancing the primary endovascular wire and the leading end of the looped wire out of the blood vessel through a second access point; and advancing a stent over the looped wire from the leading end to the target location.

In one embodiment there is provided the method described herein, further comprising: advancing the lagging end of the looped wire into the blood vessel; pulling the lagging end of the looped wire out the blood vessel through a second access point using a snare; and advancing a stent over the looped wire from the lagging end to a target location.

In one aspect there is provided a method of probing a target vessel or tract, the method comprising providing the looped wire as described herein, wherein a primary endovascular wire is threaded through the first loop of the looped wire; advancing the primary endovascular wire and the looped wire into a vessel or a tract, through a first access point; and sliding the first loop along the length of the primary endovascular wire to advance the pre-cannulation wire through the vessel or tract.

In one aspect there is provided a method of snaring, the method comprising inserting the leading end of the looped wire as described herein through a catheter from a proximal end of the catheter, wherein the one or more loops are threaded with a suture or thread, wherein at least one of the one or more loops extends out of a distal end of the catheter, and wherein a portion of the guidewire extending out of the distal end of the catheter forms a snare.

In one embodiment there is provided the method described herein, wherein the looped wire has two or more loops, wherein at least two of the two or more loops extend out of the distal end of the catheter, and wherein the segment of the guidewire between the at least two loops form the snare.

In one embodiment there is provided the method described herein, comprising pulling on the suture or thread from the proximal end of the catheter to pull the leading end of the looped wire back into the catheter.

In at least one aspect there is provided a kit comprising a suture and the looped wire.

In one aspect there is provided use of the looped wire described herein for pre-cannulating an endograft.

In one aspect there is provided use of the looped wire described herein for placing a stent.

In one embodiment there is provided the use described herein, wherein the stent is a bridging stent.

In one aspect there is provided use of the looped wire described herein, or the system described herein for treatment of an aortic aneurysm.

In one aspect there is provided use of the looped wire described herein for snaring a suture or endovascular wire.

Many further features and combinations thereof concerning embodiments described herein will appear to those skilled in the art following a reading of the instant disclosure.

DESCRIPTION OF THE FIGURES

Embodiments of devices, apparatus, methods, and kits are described throughout reference to the drawings.

FIGS. 5A to 5H are schematic illustrations showing an example method of snaring a secondary endovascular wire into the contralateral limb of a bifurcated EVAR endograft, using a looped wire having a first loop threaded with a suture. Once the free end of the secondary endovascular wire is snared and is positioned in the contralateral limb, a bridging stent can be advanced over the secondary endovascular wire and deployed in the iliac artery bridging into the contalateral gate (not shown).

DETAILED DESCRIPTION

Figure 1A:
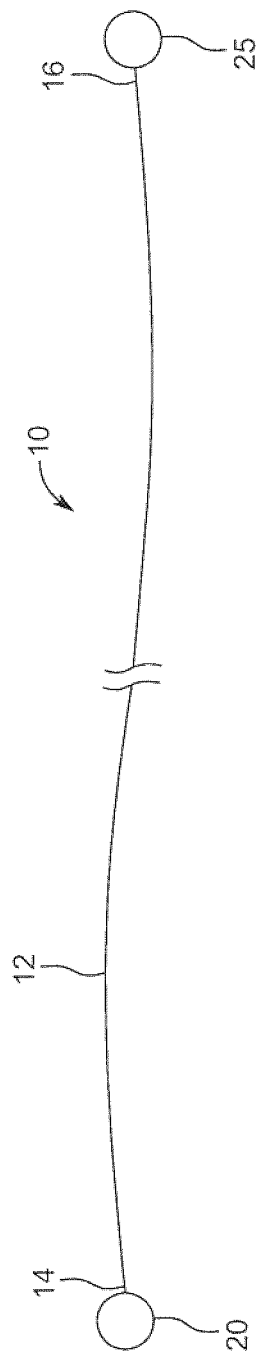
FIG. 1A is a schematic illustration showing an embodiment of a looped wire having a first and a second loop at the leading and lagging ends of the looped wire.

Numerous details are set forth to provide an understanding of the examples described herein. The examples may be practiced without these details. The description is not to be considered as limited to the scope of the examples described herein.

Endovascular repair of aortic aneurysms are particularly challenging for certain patient anatomies. Considerations include, but are not limited, the direction of a blood vessel, the relative orientation of a blood vessel, as well as the direction of blood flow can all influence the technical difficulty of placing an endograft or a bridging stent in the blood vessel. For example, advancing a covered balloon expandable stent through a downgoing branch in a branched endograft and into an upgoing blood vessel (typically an upgoing renal artery) can be difficult, if not impossible. Additional challenges are also present if the endograft is not appropriately aligned. The endograft can be misaligned if all branches or fenestrations cannot be lined up with target blood vessels, due to variations in patient anatomy. Human error plays a factor, due to limitations in fluoroscopic and angiographic guidance techniques. Blood vessel tortuosity and delivery device torqueing can also lead to misalignment. Furthermore, positioning an endograft often faces technical challenges such as wire wrapping, wire trapping on hooks, blood vessel resistance, or failure to remove the delivery catheter.

The looped wires, systems, and methods described herein are intended to reduce the execution time of endograft procedures, as well as to provide an alternative or secondary procedure for stenting if standard endovascular procedures fail to deploy a stent at the target location of a blood vessel. In current procedures, if stenting with existing endograft designs cannot be performed due to difficult anatomy or variations in anatomy, patients then require a highly invasive open surgery for aneurysm repair. Proper placement of the endograft is crucial since improper placement may result in, for example, partial or complete blockage of the endograft fenestrations or branches that can lead to tissue infarction. Endoleaks, which are leaks into the aneurysm sac after endovascular repair, are another concern that can lead to rupture.

In some embodiments, the looped wire and methods disclosed herein reduces the execution time of endovascular aneurysm repair procedures and allows for greater ease of use of current endograft systems. The looped wire is used as a pre-cannulation wire and/or for facilitating the placement of endovascular wires through fenestrations or branches prior to deployment of the endograft into the aneurysm. In an embodiment, the looped wire also acts as a guide wire for positioning a stent in a target location. These pre-cannulation wires facilitate endovascular repair of aneurysms, such as but not limited to, iliac artery aneurysms (requiring internal iliac preservation), thoracoabdominal aneurysms, and ascending or aortic arch aneurysms. One advantage of using the looped wire and methods as disclosed herein as a pre-cannulation wire for endovascular aneurysm repair is that the risk of wire wrapping is reduced or eliminated.

One system of covered stents is described in US Patent Application Publication No. 2017/0340461, the contents of which are incorporated herein by reference in its entirety. This system uses a guiding mate mounted onto the distal end portion of a delivery catheter. The guiding mate is used to thread a guiding element and thereby guiding the delivery catheter towards a distal end of the guiding element. However, such a system requires multiple tools (a catheter with a guiding mate and wire) and the endograft needs to be modified to include a guiding element that allows stenting of target vessels. The looped wires, systems, and methods described herein require minimal tools, namely the looped wire itself, and the endograft does not need to be modified to utilize the looped wire for stenting. Accordingly, the looped wires described herein can be used with commercially available endografts. Since a single tool, the looped wire, is used to accomplish multiple different actions during aneurysm repair, the overall procedure is made much simpler, which in turn reduces the time required for the procedure.

In other embodiments, the looped wire disclosed herein is used as a snare to lasso a thread, a suture, or an endovascular wire for threading the thread, suture, or endovascular wire through a cavity or lumen of a structure.

In yet other embodiments, the looped wire disclosed herein is used as a probe for introducing a medical device or tool into a lumen of a bodily structure, such as but not limited to, blood vessels, lymph vessels, the gastrointestinal tract, or the genitourinary tract.

As used herein, an "access hole", "entry point" or "access sites or point" all refer to a puncture location allowing for access into a vessel or tract, such as a blood vessel. An access site is where an endovascular wire or endograft in introduced into the blood vessel. Examples include, but are not limited to, open surgical exposure options and percutaneous options, percutaneous femoral access, percutaneous arm access (brachial artery or axillary artery), or percutaneous carotid artery access. Typically an introducer sheath is partially passed into the blood vessel through the puncture location, to allow for subsequent introduction of other devices (such as catheters, endovascular wires, and stents).

As used herein, "to advance" or "advancing" refers to passing or moving an object forward into or through a lumen (such as a blood vessel) or a tubular structure (such as a catheter). The term also refers to passing or moving a tubular structure (such as a catheter or stent) over, for example, a wire, such that the wire slides through the tubular structure acting as a track to guide the tubular structure to a target location.

As used herein, a "vessel" or a "tract" refers to a tubular structure in a body. Examples include, but are not limited to, blood vessels, lymph vessels, gastrointestinal tracts, genitourinary tracts, or respiratory tracts. References to vessels include references to tracts. Examples of blood vessels include, but are not limited to, arteries, aorta, or veins. References to "artery" should not be interpreted at limiting the application of the subject matter disclosed herein. Accordingly, references to "artery" should be interpreted to include references to any blood or fluid vessel in the body, for example, arteries, veins, or lymph vessels.

As used herein, the term "branch blood vessel" refers to a blood vessel that arises from a blood vessels splitting into a plurality of smaller blood vessels (such as the common iliac arteries), or a blood vessel that extends off from a main blood vessel (such as the renal arteries extending from the abdominal aorta).

As used herein, the term "target location" refers to any location within a vessel or tract for treatment or diagnosis. For example, a target location or vessel includes location for deployment of a stent.

As used herein, "anterior" refers to the front, while "posterior" refers to the back. These terms are anatomical terms of location used to describe the relative position of one structure to another in a patient. For example, the heart is posterior to the sternum because it lies behind it, and the sternum is anterior to the heart because it lies in front of it.

As used herein, "superior" refers to higher, while "inferior" means lower. These terms are anatomical terms of location used to describe the relative position of one structure to another in a patient, relative to a vertical axis. For example, the head is superior to the neck, while the liver is inferior to the lungs.

As used herein, "medial" refers to towards the midline, while "lateral" means away from the midline. These terms are anatomical terms of location used to describe the relative position of a structure in a patient with reference to a midline. For example, the eye is lateral to the nose, while the nose is medial to the ears.

As used herein, references to "proximal" and "distal" are relative to a user of a device. For example, a distal end of a device refers to an end that is further away from the user than a proximal end. The distal end may also be referred as a "leading" end which is inserted or advanced first into or through a vessel, while the proximal end may also be referred to as the "lagging" end following the leading end as the device is advanced through a vessel. In the context of anatomical terms of location, "proximal" and "distal" are used in structures that are considered to have a beginning and an end (such as the upper limb, lower limb and blood vessels). They describe the position of a structure with reference to its origin, where "proximal" means closer to its origin and "distal" means further away from the origin. For example, the wrist joint is distal to the elbow joint.

As used herein, a "sheath" or "introduction sheath" refers to a blunt cannula adapted for insertion into a cavity or vessel, and is used to introduce a catheter or other devices to perform endoluminal procedures. Sizes of a sheath are identified using the French scale. Appropriate sheaths and methods of using such sheaths are known and available to a skilled person.

Example catheters include, but are not limited to, angiocatheters, urological catheters, gastrointestinal catheters, neurovascular catheters, or ophthalmic catheters. These catheters are made of, for example and not limited to, silicone, nylon, polyurethane, polyethylene terephthalate (PET), latex, and thermoplastic elastomers. Example angiocatheters are 3Fr, 4Fr, 5Fr, 6Fr, 7Fr, 8Fr, 9Fr, 10Fr, 11Fr, or 12Fr, preferably 3Fr to 6Fr catheters are used. Example angiocatheters also include, but are not limited to, KMP™, SOS™, RIM™, Pigtail™, and Shepherd's hook catheters.

Endovascular wires are thin and flexible medical grade wires typically used as a guide for placement or positioning of a larger medical device, such as a catheter or a sent, in a patient. Standard endovascular wires come in two basic configurations: solid steel or nitinol core wires and solid core wire wrapped in a smaller wire coil or braid. Coiled or braided wires offer a large amount of flexibility, pushability and kink resistance. As used herein, the term "pushability" is defined as the ability to transmit force from the proximal end of a wire or catheter to the distal end. As used herein, the term "kink resistance" refers to a property of a wire or catheter that tends to avoid forming into tight curl, twist, or bend.

One example endovascular wire is a wire from Boston Scientific™ which uses a nitinol tube with micro-cut slots instead of braided wire to improve torque control. Nitinol wire, used by itself or braided with stainless steel, helps increase flexibility and allows the wire to spring back into shape after navigating a tortuous vessel segment. The Cook Medical™ amplatzer wire or lunderquist wire is another example of an endovascular wire. Some endovascular wires are coated with a polymer, such as silicone or polytetrafluoroethylene (PTFE), to increase lubricity. Hydrophilic coatings reduce friction during positioning and for easier movement in tortuous vessels. Wire diameters are measured in thousandths of an inch, usually between 0.014 and 0.038 inches. Lengths are measured in centimeters, ranging from 80 to 450 cm.

As used herein, the term "threading" refers to passing a thread, a suture, an endovascular, or similar thread-like material, through an opening.

As used herein, "pre-cannulate" or "pre-cannulation" refers to threading a wire or a number of wires through the fenestrations or branches, or other openings, of an undeployed endograft during the manufacturing process of an endograft or after the manufacturing process just prior to insertion of the endograft into a patient through pre-cannulation tubes such as in the Gore TAMBE™ device. Typically pre-cannulated wires are used in a through-and-through access technique but are not limited to this.

As used herein, a "stent" or a "stent graft" is a tubular support structure inserted into the lumen of an anatomic vessel or duct to keep the passageway open, and the term "stenting" refers to placement of a stent. One example of a stent is an aortic stent graft or an "endograft" typically used in EVAR procedures. An endograft is a fabric covered metallic stent intended for insertion and deployment at an aortic aneurysm. Example endografts include, but are not limited to, the Gore Medical™ (Flagstaff, Arizona, USA) Thoracoabdominal Branch Endoprosthesis (TAMBE™ device), iliac branch graft devices such as the Gore Iliac Branch Endoprosthesis™ or the Cook Zenith™ Iliac branch graft, or aortic arch aneurysm branch devices. Examples of current endovascular aneurysm repair procedures using some of these endografts is disclosed in https://www.gore-medical.com/video/brightcove/excluder-iliac-branch-endo-prosthesis-animation-video and https://www.cookmedi-cal.eu/products/e2f94fbc-c83e-459e-9caf-aee8bd245cb7/ the disclosures of which is incorporated herein by reference in its entirety.

Some endografts have one or more holes or "fenestrations" on the graft body to maintain the patency of branch blood vessels extending from the stented blood vessel. For example, an endograft may be attached to the abdominal aorta with one fenestration positioned over the opening to each of the renal arteries, thereby allowing blood flow to the kidneys. Some endografts have one or more "branches", that extend from a "main body stent", or a main portion, of the endograft. The branches are intended to be portals for other stents to be deployed from the main body stent into each branch blood vessel. Some endografts have both fenestrations and branches.

As used herein, a "bridging stent" refers to a stent that is used for stenting a branch blood vessel and for connecting to a fenestrated or branched endograft. A bridging stent is deployed separately from the endograft, with at least one end in fluid communication with the main body stent of the endograft so as to allow for blood flow to the branch blood vessel. In some cases, a bridging stent is introduced through a different access point and blood vessel than the one use to advance the endograft. One example of a typical bridging stent is a covered balloon-expandable of self-expanding stent.

As used herein, the term to "deploy" or "deployment" of a stent refers to releasing a stent from its cover or by other mechanisms so as to allow the stent to expand and stent a vessel. Typically, deployment of a stent is irreversible.

Looped Wire Embodiments

In some embodiments, the looped wire described herein is intended for facilitating the placement of an endograft into a blood vessel. The blood vessel can be an artery, such as the aorta. In an embodiment, the looped wire facilitates placement of an endograft into the aortic arch or the abdominal aorta.

The looped wire comprises a flexible guidewire having a leading end and a lagging end and one or more loops distributed along the length of the guidewire. The lengths of the guidewire are not limited by the embodiments described herein, but may come in various lengths depending on the application. For example, in some embodiments, the guidewire is 200 cm, 250 cm, 300 cm, 350 cm, or 400 cm long. In one embodiment, the guidewire is 300 cm long. The guidewire is flexible and kink resistant, and requires minimal pushability for advancing itself through a blood vessel. In one embodiment, the guidewire is a nitinol guidewire The guidewire has a diameter of about 0.014 inches, 0.018 inches, 0.025 inches, or 0.035 inches In a preferred embodiment, the guidewire has a diameter of about 0.018 inch. In one embodiment, the guidewire is an endovascular wire. In another embodiment, the guidewire is a hybrid wire made of part endovascular wire and part suture material, which is used in circumstances where greater flexibility is desired. For example, a hybrid guidewire or a guidewire made of a suture material is more advantageous when advancing catheters over the guidewire at sharper or more acute angles that what standard wires allow. Optionally, the guidewire is hollow.

The looped wire disclosed herein is intended for threading a thin strand of material through the one or more loops, and for sliding the one or more loops and in turn the looped wire along the length of the strand of material. For example, the strand of material is an endovascular wire, a suture, a thread, or any thread-like material. Each of the one or more loops has an inner diameter that is greater than the thickness of, for example, an endovascular wire, so that the endovascular wire can be threaded through the one or more loops. The diameter of each of the one or more loops also needs to be small enough such that the looped wire maintains a low overall profile. However, the diameter is also large enough such that a catheter or sheath can push the one or more loops along the length of the endovascular wire, while advancing the catheter or sheath over the endovascular wire. Therefore, in preferred embodiments, the one or more loops have an inner diameter that is about 0.002 to 0.003 inches larger than the diameter of the endovascular wire.

In a preferred embodiment, the one or more loops have an inner diameter of about 0.038 inches for threading a 0.035 inch endovascular wire through the one or more loops. In another preferred embodiment, the one or more loops have an inner diameter of about 0.040 inches for threading a 0.038 inch endovascular wire through the one or more loops. The specific sizes and dimensions of the loops are not limited by the embodiments described herein, but may be sized and shaped based on the particular endovascular wires and catheters used in the endovascular aneurysm repair procedures.

In some embodiments, the looped wire has a plurality of loops. In one embodiment, the looped wire has a first loop located proximate to the leading end of the guidewire, and preferably at the leading end of the guidewire. In another embodiment, the looped wire has a second loop located proximate to the lagging end of the guidewire, preferably at the lagging end of the guidewire. Turning to FIG. 1A, an embodiment of a looped wire 10 is shown, having a circular first loop 20 at the leading end 14 of a nitinol guidewire 12 and a circular second loop 25 at the lagging end 16 of the guidewire 12. The loops 20 and 25 are generally circular or elliptical, but can also be of any shape that allows for sliding along the length of an endovascular wire. The loops have an inner diameter ($d_i$) of 0.038 inches for threading through a 0.035 inch endovascular wire (see FIG. 1C). The loop can be made of the same material as the guidewire, for example nitinol, or a different material than the guidewire.

Figure 1B:
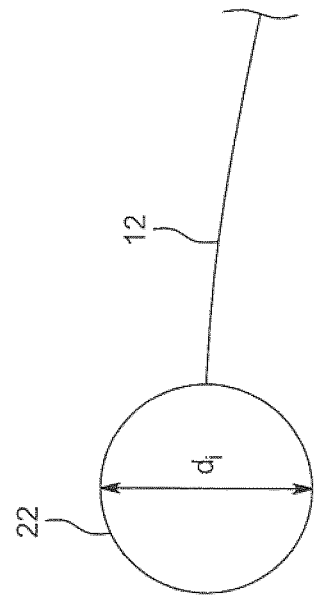
FIG. 1B illustrates an enlarged view of the first loop in a compressed state. The double-headed arrow indicates an outer diameter ($d_o$) of the first loop.
Figure 1C:
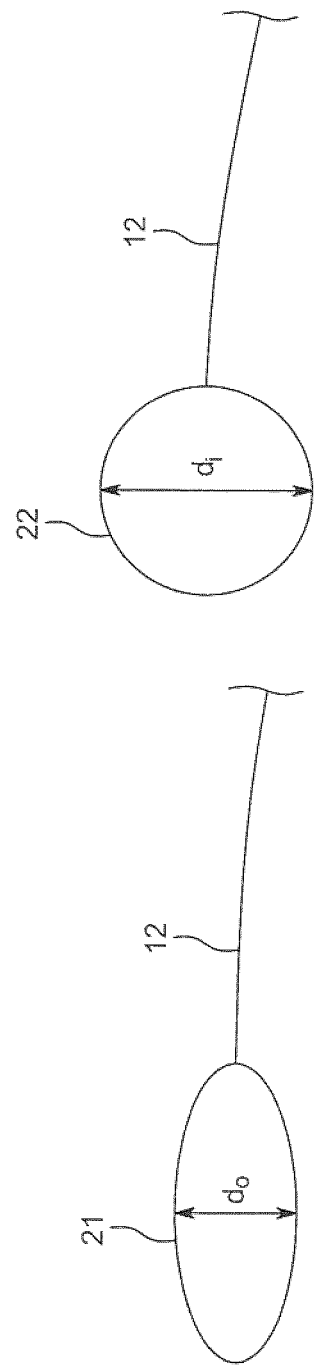
FIG. 1C illustrates an enlarged view of the first loop in a non-compressed state. The double-headed arrow indicates an inner diameter ($d_i$) of the first loop. The broken away lines illustrated in FIG. 1A show that the looped wire is of various lengths.

In some embodiments, the one or more loops are flexible ellipses that are compressible into a compressed state for inserting the looped wire through a catheter. As shown in FIGS. 1B and 1C, the first loop is compressible from a non-compressed state 22 having a sufficient inner diameter for threading an endovascular wire or suture through and for sliding along the length of the endovascular wire or suture, to a compressed state 21 having sufficiently small outer diameter ($d_o$) for inserting the looped wire through a catheter. In one embodiment, the one or more loops have an outer diameter of less than 0.035 inches, less than 0.030 inches, or less than 0.025 inches for insertion through a 0.035 inch catheter. Various other outer diameters are possible in the compressed state, as long as the outer diameters of the one or more loops in the compressed state are less than the diameter of the catheter lumen.

Optionally, the one or more loops are open loops, each having a fastening means for opening and closing the loops. For example, the open loops are pliable and can be bent into a closed loop, or the open loops comprise hooks on the open end of the loops for hooking the loops closed. The open loops can also be opened and closed by other mean known to a person skilled in the art. Optionally, the one or more loops are detachable from the guidewire where, for example, the one or more loops are attached to the guidewire by complementary screw and thread mechanism. Other designs for the detachable attachment of the one or more loops to the guidewire is known to a person skilled in the art.

In some embodiments, the first and/or second loops 20, 25 are formed by bending the leading and/or lagging ends 14, 16 back on itself and attaching the ends to the guidewire 23 to form a ring or a noose. A coil around the wire, such as a platinum coil, can be used to keep the loop in the closed position. Alternatively, the first and/or second loops 20, 25 are manufactured separately from the guidewire 12 and affixed onto the guidewire. Optionally, the one or more loops can be attached to the guidewire at an angle to facilitate sliding of the one or more loops along the length of, for example, an endovascular wire.

In one embodiment of the looped wire 10, the leading end 14 of guidewire 12 comprises a floppy tip. The floppy tip extends about 10 cm, 15 cm, 20 cm, 25 cm, or 30 cm from the leading end 14 of the guidewire 12. Preferably, the floppy tip extends about 20 cm from the leading end 14 of the guidewire 12. The floppy tip is intended to assist in navigating the looped wire through various vessel anatomies, and has greater flexibility than the rest of the guidewire. In some embodiments, the tip is made floppy by heating up an end portion of the nitinol guidewire to soften the guidewire. Alternatively, in other embodiments, an end potion (for example, 20 cm from the leading or lagging end) of the guidewire is ground down so that it is tapered over the length of this end portion. The thinned end portion of the guidewire is more floppy than the rest of the guidewire, thereby creating a floppy tip. One of the advantage of having a floppy tips is that a stiffer guidewire can be used for support and guiding a stent to a target location, while the flexibility of the floppy tip allows atraumatic advancement or introduction of the looped wire through a blood vessel. Either the leading or lagging end of the looped wire, can be made floppy. The lagging end is preferably made floppy, for example, when the looped wire is used as a snare during an endovascular procedure, so that the looped wire can bend on itself and fit through a sheath.

In one embodiment of the looped wire, used for pre-cannulation, the guidewire is a PTFE coated nitinol wire having 0.018 inches in diameter and measuring 300 cm. One or both of the leading and lagging ends of the guidewire are tapered down to 0.005 inches in diameter to form a floppy tip, and the one or both ends are further looped on itself to form a loop. The loop is held in place with a platinum coil. Optionally or in addition, the distal 40 cm of the leading end is heated to soften the wire.

Endograft Systems with Looped Wires

The looped wires described herein are intended for use together with endografts for endovascular aneurysm repair. In an embodiment, one or more looped wires are threaded through the fenestrations or branches of an endograft before or after deployment of the endograft. This configuration is particularly useful for thoracoabdominal branch devices. The Gore TAMBE™ (Thoracoabdominal Branch Endoprosthesis) is one example system that benefits from pre-cannulating with the looped wire as described herein.

Figure 2:
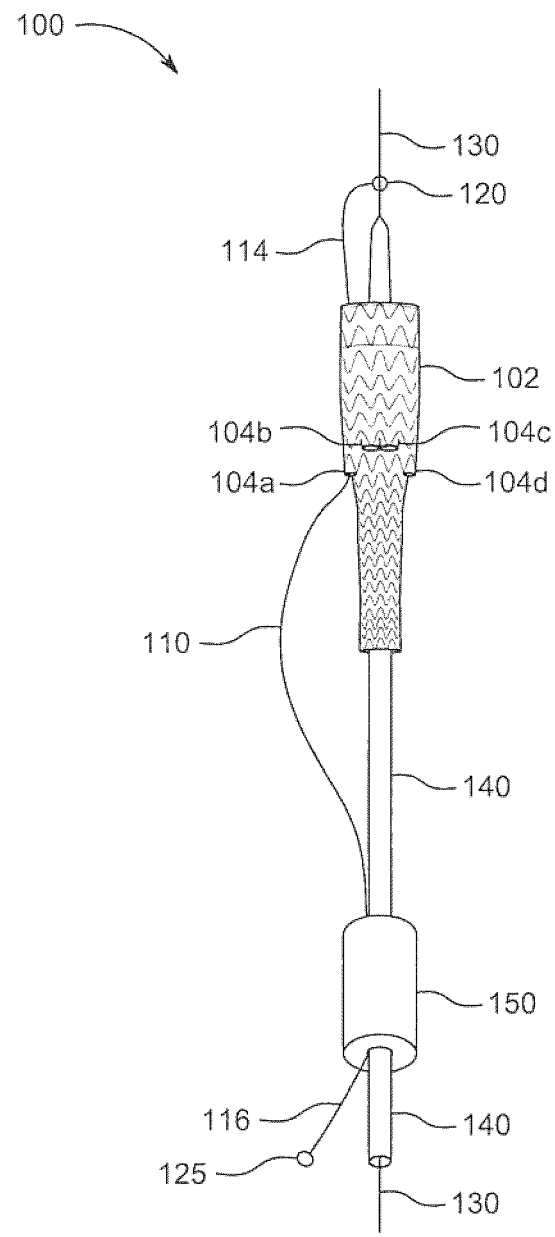
FIG. 2 is a schematic illustration showing an embodiment of an endograft system having one looped wire with two loops, one on each end, and anchored to a main endovascular wire. The endograft is a deployed branched thoracoabdominal aneurysm stent graft. The looped wire is threaded through the main body stent and exits through one of the branches of the endograft.

Turning to FIG. 2, a pre-cannulated endograft system 100 is shown comprising a deployed branched endograft 102 or a branched aneurysm stent graft that is pre-cannulated with a looped wire 110. The system 100 also includes a deployment catheter 140 for deploying the endograft 102, and a sheath 150 for placement at an access point in the blood vessel for subsequent introduction of other devices. The looped wire 110 has a first loop 120 at the leading end 114 of the wire, and the first loop 120 is threaded and anchored onto a primary endovascular wire 130. The primary endovascular wire is used for advancing the endograft to a target location. One of the branches 104a is pre-cannulated with the looped wire 110. The looped wire extends from where it is anchored to the primary endovascular wire 130, through the main body stent of the branched endograft 102, and out through branch 104a. The other branches 104b, 104c, and 104d can similarly be pre-cannulated with separate looped wires (not shown). The looped wire 110 has a second loop 125 at the lagging end of the wire 116. This second loop 125 can be used to facilitate bridging stent placement as described in Example 3. Similar configuration or arrangement is used for fenestrated endografts.

Figure 3B:
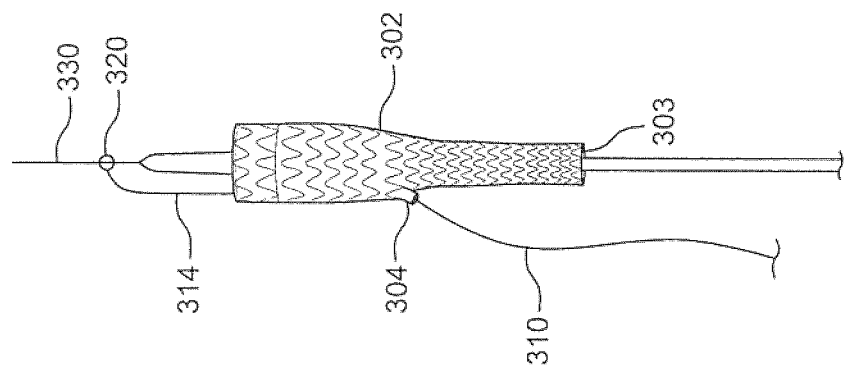
FIG. 3B is a schematic illustration showing an alternate configuration for pre-cannulating an endograft with a looped wire.
Figure 3A:
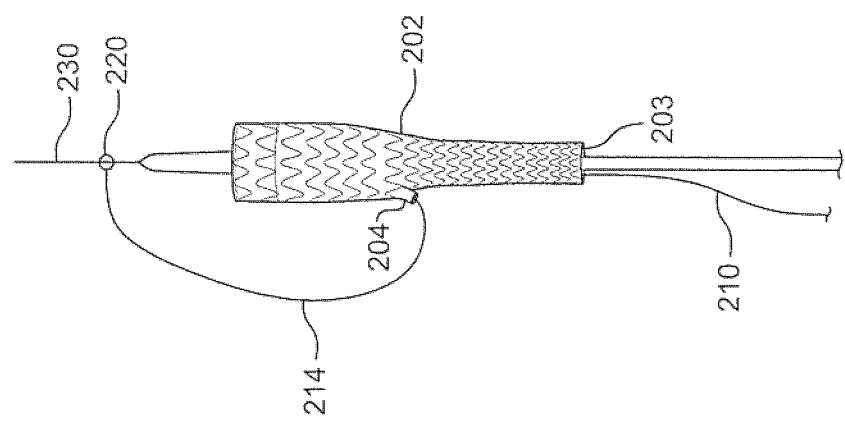
FIG. 3A is a schematic illustration showing an example configuration for pre-cannulating a branched endograft with a looped wire.

In some embodiments, the looped wire 210 can be threaded through the main body stent 203 of a branched endograft 202, and out through a branch 204 to facilitate, for example, an arm approach to place bridging stents (see FIG. 3A). A first loop 220 at the leading end 214 of the looped wire 210 is anchored to the primary endovascular wire 230. This configuration is compatible with the current Gore TAMBE™ device. An alternate embodiment is shown in FIG. 3B, where the looped wire 310 is threaded from the outside of a branched endograft 302, through a branch 304 and into the main body stent 303 to facilitate, for example, a femoral approach for placing the bridging stent. A first loop 320 at the leading end 314 of the looped wire 310 is anchored to the primary endovascular wire 330. Preferably, the first loop 220 or 230 are threaded onto the primary endovascular wire 230 or 330 ahead of the endograft 202 or 203. Similar configurations or arrangements are used for fenestrated endografts.

One pre-cannulated fenestrated endograft system is described in Joseph, G. et al. "Externalized Guidewires to Facilitate Fenestrated Endograft Deployment in the Aortic Arch", J Endovasc Ther. 2016 February; 23(1): 160-171, the disclosure of which is incorporated herein by reference in its entirety. This endograft system uses externalized guidewires to facilitate aortic arch endovascular repair. However, the endovascular repair techniques of Joseph et al. does not reduce or eliminate wire wrapping. If more than one fenestration is pre-cannulated using their technique then wire-wrapping and entanglement would become a major issue. The looped wires, systems, and methods described herein are intended for reducing or eliminating wire-wrapping, and at the same time accommodate pre-cannulation of multiple branches or fenestrations. By providing an endograft having fenestrations and/or branches pre-cannulated with multiple looped wires, this enables the treatment of more complicated aneurysms and overall makes the procedures simpler with reduced time and less complications for patients.

Where the endograft is pre-cannulated with multiple looped wires each having a first loop at the leading end, the first loops are threaded onto the primary endovascular wire based on the order of use. For example, the most distally anchored first loop is the first one to be used or removed from the endovascular wire. This process is repeated for as many branches or fenestrations as needed. This process can be performed prior to the stent graft or endograft being sheathed or constrained for delivery, or after deployment. Once all of the first loops of the looped wires have been positioned as described above, the stent graft or endograft is advanced over the primary endovascular wire. As the stent graft or endograft is advanced forward, the tapered tip of the graft pushes the freely moving first loops up the primary endovascular wire, sliding the looped wires distally forward. One advantage of pre-cannulating an endograft with one or more looped wires is that these looped wires allow the endograft to rotate or twist as much as needed for adjustment and positioning of the endograft and for aligning the fenestrations or branches with the branch blood vessels without wire-wrapping or entanglement of wires. The looped wires are also anchored to the primary endovascular wire, and therefore do not inadvertently fall out of the fenestrations or branches. Furthermore, the pre-cannulation configuration described above allows the endograft to maintain an extremely low profile when advanced through blood vessels. Maintaining a low-profile is extremely important given that many currently used endografts have large profiles.

In an embodiment, an endograft is provided in a delivery system by first pre-cannulating the endograft with one or more looped wires as described herein and then compressing or sheathing the endograft. By providing the endograft delivery system with the endograft pre-cannulated, the one or more looped wires are already in position for use when the endograft is deployed in an aneurysm. Such an endograft delivery system is beneficial since it reduces endovascular aneurysm repair procedure time, improves accuracy and efficiency of aligning fenestrations and branches with branch blood vessels, as well as prevents wire tangling. The delivery system comprises the endograft, a primary endovascular wire extending through a main body stent of the endograft, and one or more looped wires each anchored to the primary endovascular wire by a first loop at the leading end of the looped wire and in sliding engagement with the primary endovascular wire. The endograft has one or more fenestrations and/or branches, and the one or more looped wires extend through the main body stent of the endograft and out through the one or more fenestrations and/or branches. In some embodiments, only some of the fenestrations and/or branches are pre-cannulated with looped wires. In other embodiments, all the fenestrations and/or branches are pre-cannulated with looped wires. In a preferred embodiment, each fenestrations and/or branches are pre-cannulated with one looped wire per fenestration and/or branch. In an alternative embodiment, each fenestration and/or branched is pre-cannulated with one or more looped wires. In some embodiments, each or at least one of these looped wires further comprises a second loop at the lagging end of the looped wire.

EXAMPLES

Example 1

Pre-Cannulation with Looped Wires

Figure 4A:
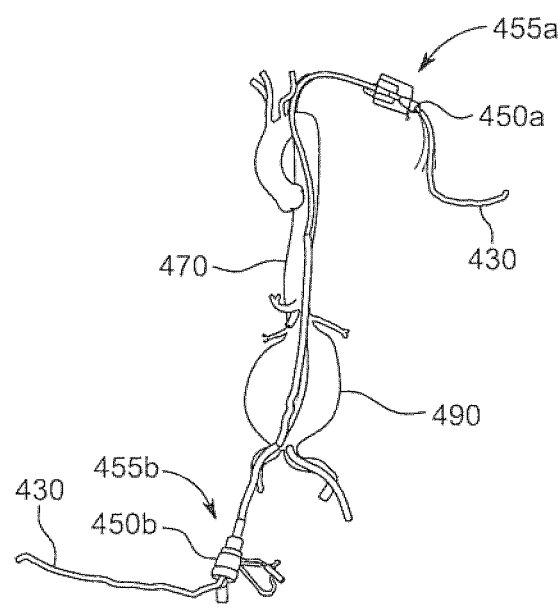
FIGS. 4A to 4F are schematic illustrations showing an example pre-cannulation method, using a first looped wire inserted through a first access point to facilitate insertion of an endograft and a plurality of other looped wires through a second access point.
Figure 4B:
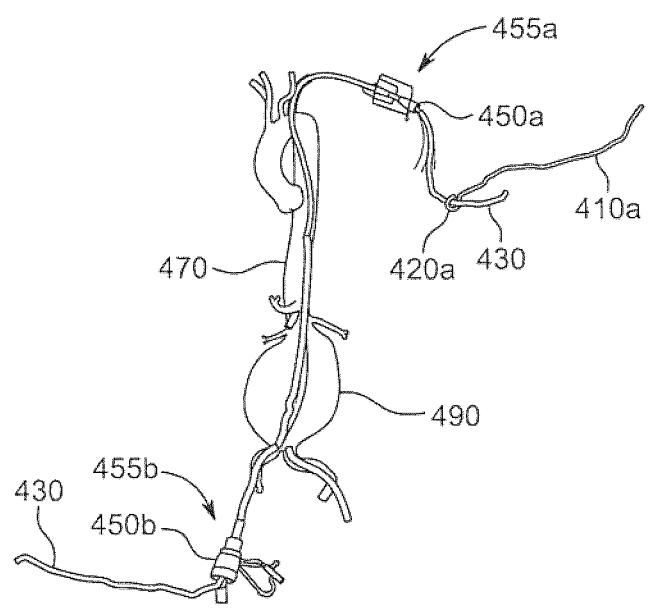
Figure 4C:
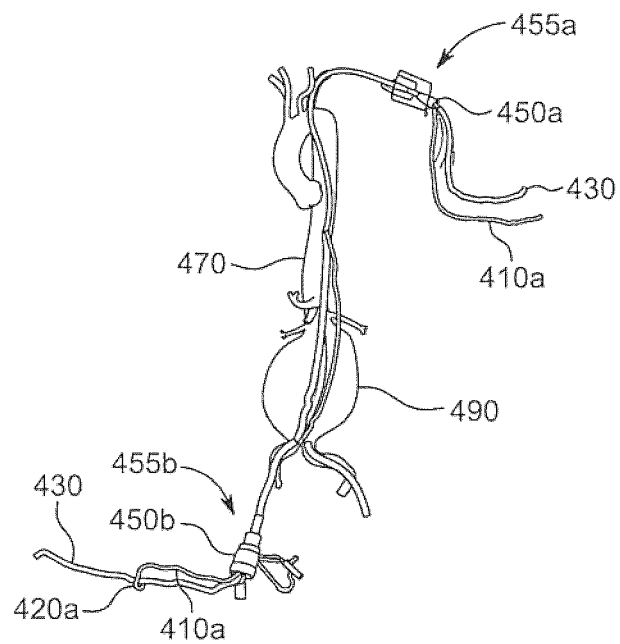
Figure 4D:
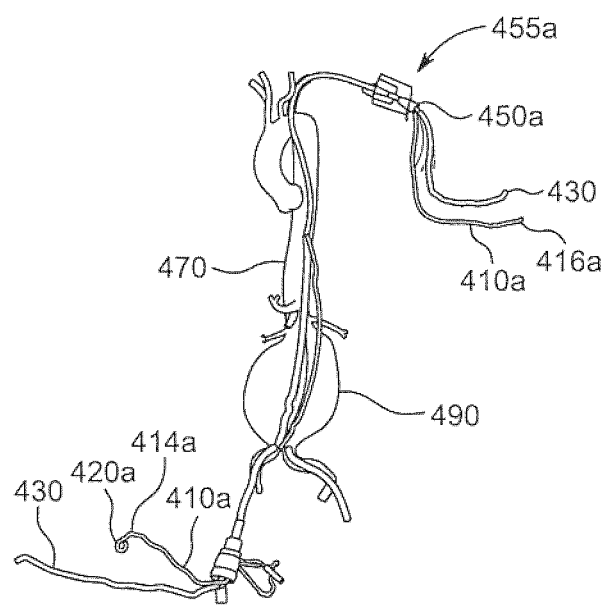

A through-and-though primary endovascular wire 430 was separately placed from femoral access point 455*b* and sheath 450*b*, and out through the upper extremity access point 455*a* and sheath 450*a* in a "body-floss" configuration (see FIG. 4A). The primary endovascular wire 430 passes through a segment of the aorta 470, and through an aneurysm in the aorta 490. An endograft may also be separately deployed using this primary endovascular wire 430 (not shown). A first looped wire 410*a* was threaded onto this primary wire 430 extending out of the upper extremity access point 455*a*, by threading a first loop 420*a* of the first looped wire 410*a* onto the primary wire (see FIG. 4B). The first looped wire 410*a* was inserted through the upper extremity access point 455*a* and advanced out of the body through the femoral access point 455*b* by sliding the first looped wire 410*a* along the primary wire 430 (see FIG. 4C). The looped wire 410*a* is unthreaded from the primary wire 430 by sliding the first loop 420*a* off the primary wire from its free end extending out of the femoral access point 455*b* (see FIG. 4D).

At this point, a catheter and/or an endovascular wire can then be placed or passed over the first looped wire 410*a* from its lagging end 416*a*, and inserted into the aorta from the upper extremity access point 455*a* wire to facilitate antegrade placement of a stent, such as a bridging stent, if an endograft was previously deployed using the primary wire. For example, a catheter was passed over the first looped wire 410*a* from the upper extremity access point 455*a* until a target location (such as a fenestration or a branch of an endograft) was reached. The first looped wire 410*a* was then removed from the catheter. A secondary endovascular wire was then inserted through the catheter from its free end at the upper extremity access point 455*a*, and the catheter was withdrawn out of the body from the upper extremity access point 455*a* leaving behind the secondary endovascular wire with its distal end positioned at the target location. A stent was advanced over the catheter or the secondary endovascular wire until the target location was reached and then deployed to stent the target location.

Alternatively, a long catheter was placed over the first looped wire 410*a* from its leading end 414*a*, and inserted into the aorta from the femoral access point 455*b* and out through the upper extremity access point 455*a*. The first looped wire 410*a* was removed out of the body and replaced with a secondary endovascular wire by inserting the secondary endovascular wire through the long catheter to facilitate stent placement, such as a bridging stent in a similar manner described above. The process was repeated for however many branches or fenestrations require bridging stents are stented.

Figure 4E:
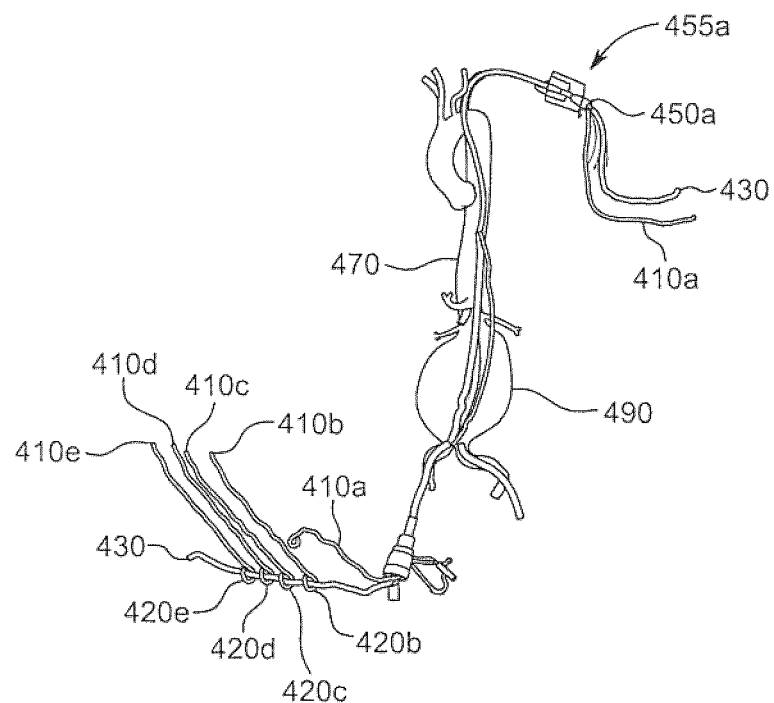
Figure 4F:
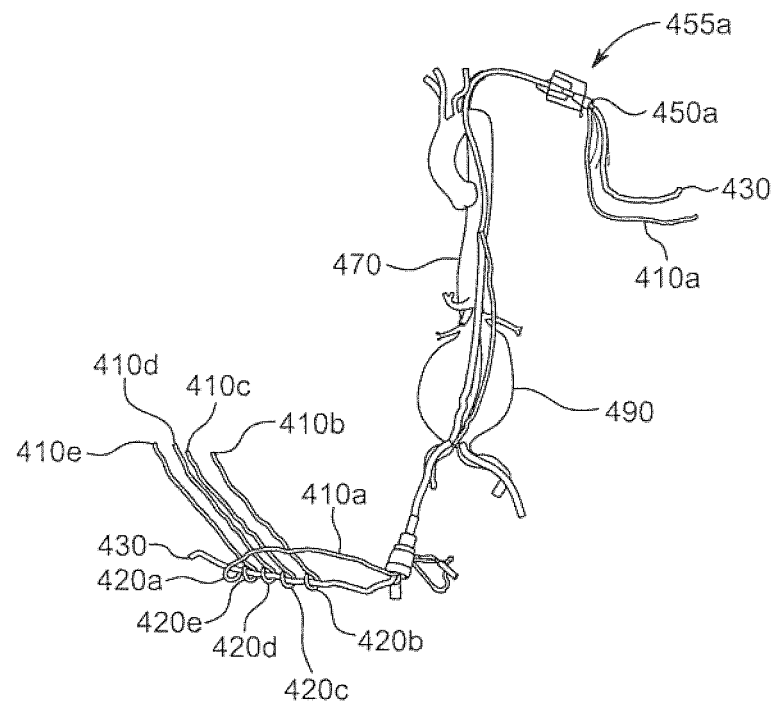

In another example pre-cannulation procedure, after the looped wire 410*a* was unthreaded from the primary wire 430, four other looped wires 410*b*, 410*c*, 410*d*, and 410*e* were threaded onto the primary wire 430 extending out of the femoral access point 455*b*, by threading the respective first loops 420*b*, 420*c*, 420*d*, and 420*e* (see FIG. 4E). In some cases, these four looped wires 410*b*, 410*c*, 410*d*, and 410*e* are those used to pre-cannulate an endograft as illustrated in for example in FIG. 2, where the lagging ends of these four looped wires are threaded through fenestrations or branches of the endograft. To advance the four looped wires 420*b*, 420*c*, 420*d*, and 420*e* (and in some cases also the endograft pre-cannulated by these four looped wires) into the aorta through the femoral access point 455*b*, the first looped wire 410*a* was threaded back onto the primary endovascular wire 430 behind the first loops 420*b*, 420*c*, 420*d*, and 420*e*. The first looped wire 410*a* was then pulled from its lagging end 416*a* extending out of the upper extremity access point 455*a*, thereby pulling the four looped wires 410*b*, 410*c*, 410*d*, and 410*e* along the primary endovascular wire 430.

Example 2

Contralateral Gate Cannulation of a Bifurcated Endograft

Figure 5D:
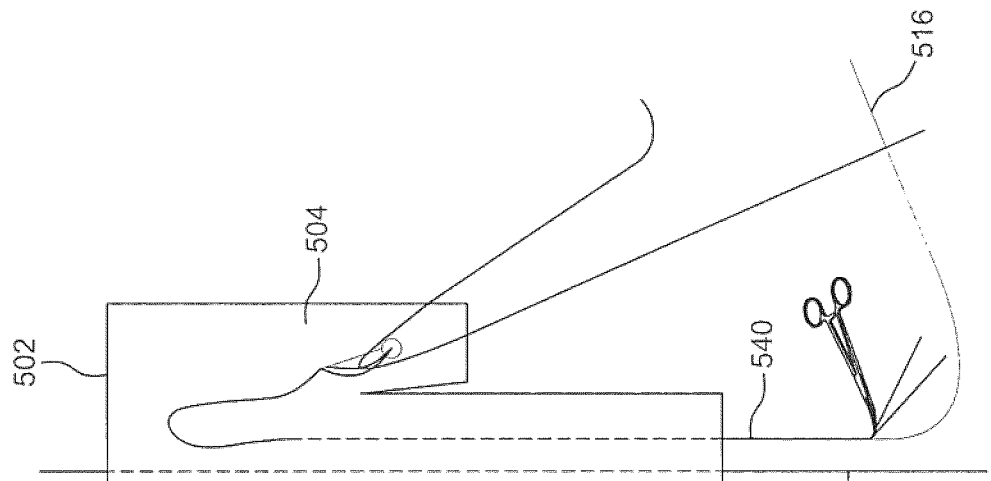
Figure 5E:
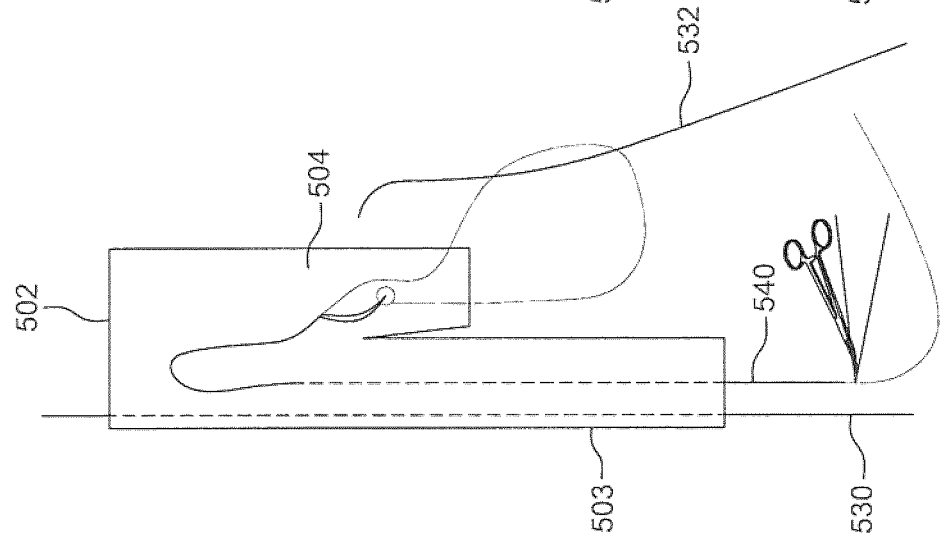
Figure 5F:
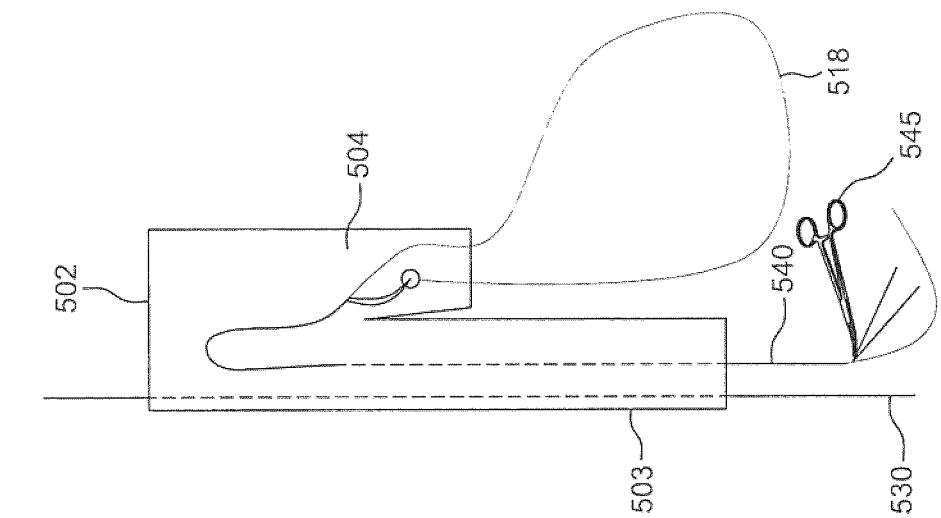
Figure 5H:
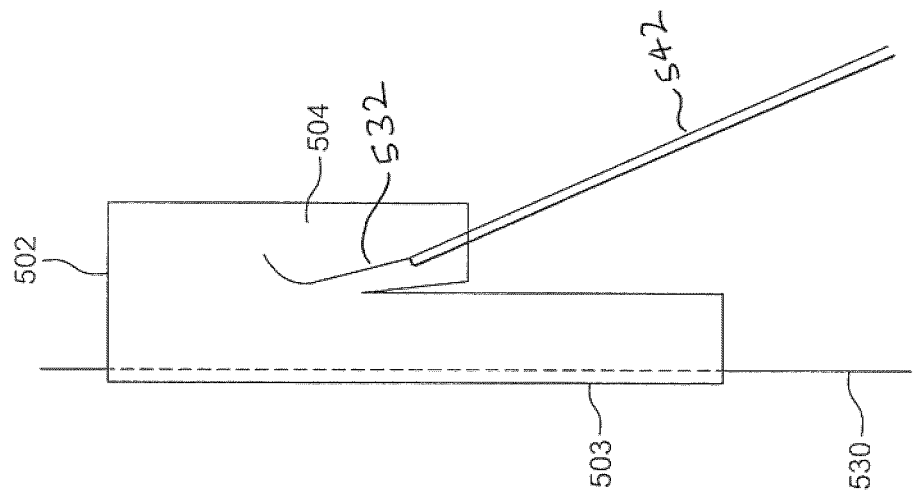
Figure 5G:
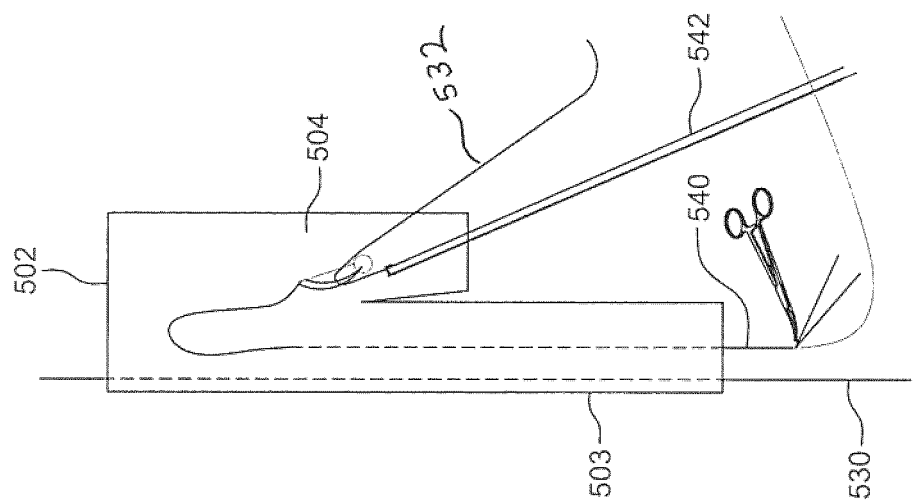

A looped wire 510 was used to thread a secondary wire 532 through the contralateral limb 504 of a bifurcated EVAR endograft 502. As shown in FIG. 5A, the endograft 502 has a reverse curve catheter 540 extending through the main body stent 503 and into the contralateral limb 504. The free end of the catheter 540 terminates in the contralateral limb 504. The endograft 502 was placed into position by advancing the endograft over a primary endovascular wire 530. A suture 560 was threaded through a first loop 520 on the leading end 514 of the looped wire 510 (see FIG. 5B). This looped wire 510 was inserted through the catheter into the main body stent 503 and around into the contralateral limb 504, such that the leading end 514 and the first loop 520 extended out of the free end of the catheter 540 (see FIG. 5C). The suture was then locked into place using a hemostat 545, such that the first loop 520 remained in a fixed position relative to the free end of the catheter 540. The looped wire 510 was further inserted through the catheter to so that a length of the looped wire 510 extends out of the free end of the catheter 540 to form a large loop or a snare 518 (see FIG. 5D). A secondary endovascular wire 532, inserted from a separate access point, was captured by the snare 518 (see FIG. 5E). The looped wire 510 was then pulled from its lagging end 516 tightening the snare, until a segment of the secondary endovascular wire 532 was pulled into the contralateral limb 504 adjacent the free end of the catheter 540 (see FIG. 5F). A second catheter 542 was advanced over the secondary endovascular wire 532, until the distal end of the second catheter 542 was positioned in the contralateral limb 504 (see FIG. 5G). At this point, the secondary endovascular wire 532 was pulled from the proximal end of the second catheter 542, until the free end of the secondary endovascular wire 532 extended into the contralateral limb 504 (see FIG. 5H). With the secondary endovascular wire 532 in the configuration as illustrated in FIG. 5H, a bridging stent can now be advanced over the secondary wire and a bridging stent can be placed in the iliac artery extending into the contralateral limb 504.

Similar procedures can also be used for other applications where the looped wire is used as a snare.

Figure 8:
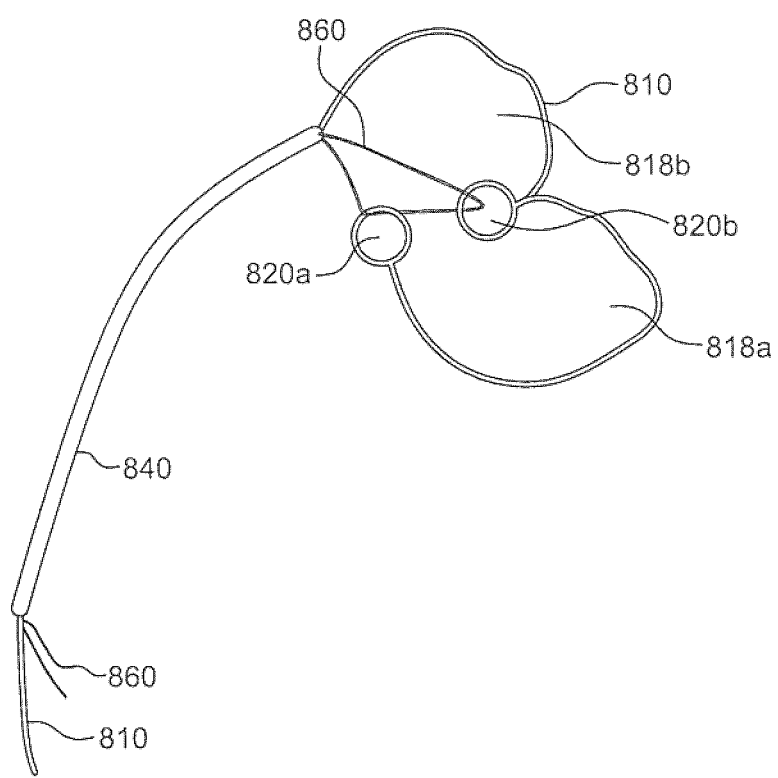
FIG. 8 is a schematic illustrations showing an alternate example looped wire and method for snaring a endovascular wire.

One variation of the above procedure uses a looped wire 810 with a plurality of loops, as shown in FIG. 8. A single suture 860 was threaded through the plurality of loops 820*a* and 820*b*, such that when this looped wire was inserted through a catheter 840 and out of the free end of the catheter, each segment 818*a* and 818*b* of the guidewire between each adjacent loops formed a snare. This allows more snares to be deployed at the same time, thereby increasing the chances of snaring a wire.

Example 3

Looped Wire with Two Loops for Bridging Stent Placement

Figure 6B:
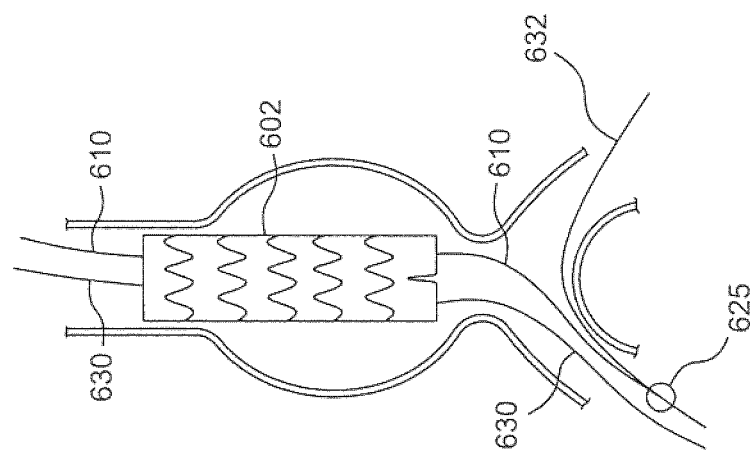
FIGS. 6A to 6D are schematic illustrations showing an example method of stenting a thoracoabdominal aneurysm with a branched endograft. A looped wire with first and second loops are used to facilitate deployment of a bridging stent.
Figure 6A:
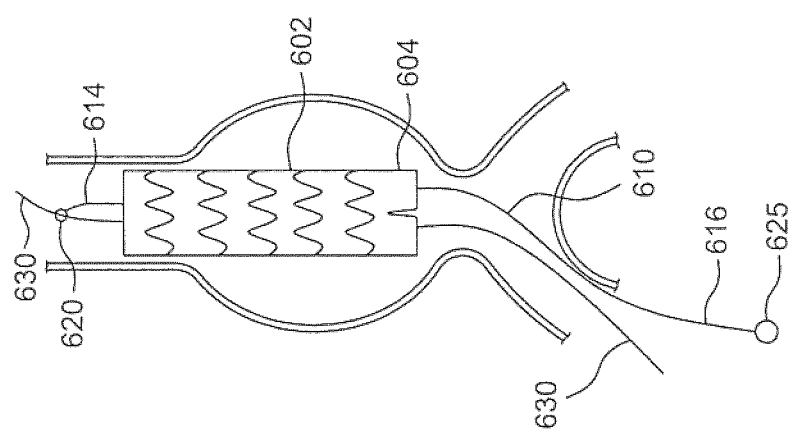
Figure 6D:
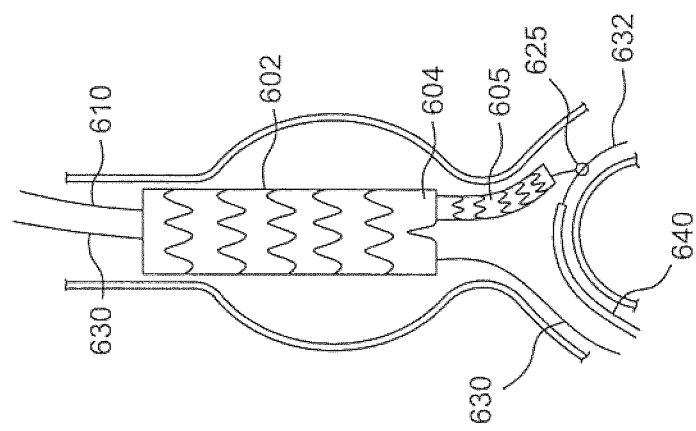
Figure 6C:
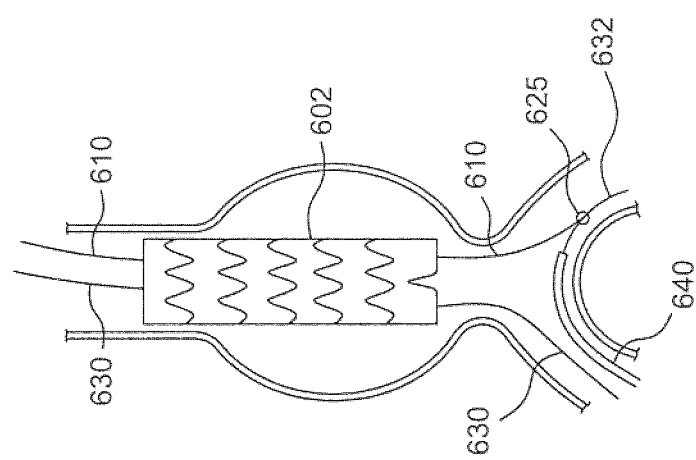

In this example, a looped wire 610 has a first loop 620 at its leading end 614 and a second loop 625 at its lagging end 616. This example procedure was used for treating patients with thoracoabdominal aneurysms with a branched endograft 602 pre-cannulated with the looped wire 610, which extends through a branch 604 of the endograft 602. A primary endovascular wire 630 was passed from a femoral access point to an upper extremity access point in a "body floss" configuration as described in Example 1 (see FIG. 4A for this configuration). The branched endograft 602 with looped wire 610 was advanced over this primary endovascular wire 630 and deployed (see FIG. 6A). The leading end 614 of looped wire 610 was pushed out of the upper extremity access sheath from the femoral artery access sheath (as described above in Example 1). A secondary endovascular wire 632 was advanced from the femoral access point and directed to a target vessel in a retrograde fashion. In some cases, the secondary endovascular wire 632 was advanced from the femoral access point, through a target vessel, and out through a third access point. The second loop 625 of the looped wire 610 was threaded onto the secondary endovascular wire 632 extending out of the femoral access point. The looped wire 610 was then pulled from the upper extremity access point to advance the lagging end 616 of the looped wire 610 into the femoral access point, the second loop 625 sliding along the length of the secondary endovascular wire 632 (see FIG. 6B). In some cases, a catheter 640 was advanced over the secondary endovascular wire 632 from the femoral access point, to push the second loop 625 along the length of the secondary endovascular wire 632 to a target location in the target vessel (see FIG. 6C). Alternatively, a low profile sheath can be used instead of catheter 640. Since the second loop 625 is anchored or threaded to the secondary endovascular wire 632, the position of the second loop 625 is dictated by the secondary endovascular wire 632. Furthermore, by having the looped wire 610 anchored to the secondary endovascular wire 632 by the second loop 625, this prevents the looped wire 610 from slipping off when a stiff device (such as an expandable balloon or a self-expanding covered bridging stents and sheaths) are advanced over the looped wire 610 from its leading end 614 and into the target vessel. As shown in FIG. 6D, a bridging stent 605 was advanced from the upper extremity access point over the looped wire 610, through branch 604 of the endograft 602, and to the target vessel. The bridging stent 605 was then deployed, with one end of the bridging stent 605 attached to the branch 604 of the endograft 602. One the bridging stent 605 was deployed, the secondary endovascular wire 632 was pulled out of the target vessel releasing the second loop 625. This releases the looped wire 610, which can then be removed from the upper extremity access point. This process was repeated for the other target vessels as required. This procedure allows for efficient stenting of challenging blood vessels to be stented during endovascular aneurysm repairs Example 4

Aortic Arch Endograft

Figure 7A:
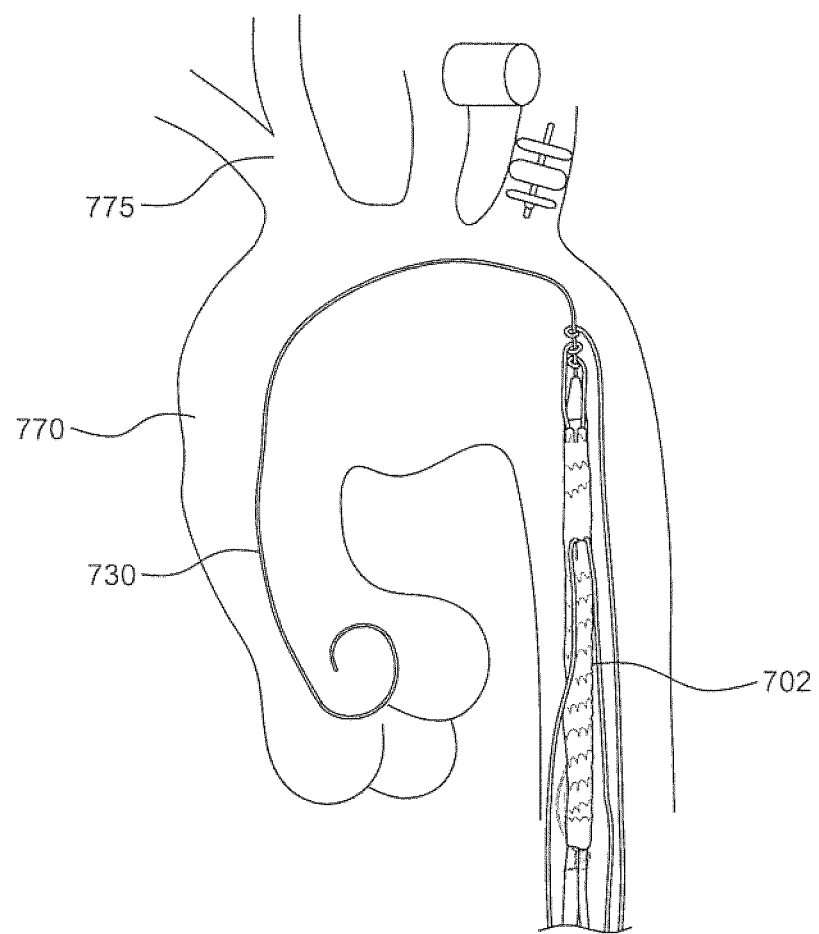
FIGS. 7A to 7F are schematic illustrations showing an example method of stenting the aortic arch using an endograft pre-cannulated with three looped wires. The looped wires facilitate bridge stenting of two branch vessels extending from the aortic arch. A carotid-subclavian bypass with embolization of the proximal left subclavian is shown.
Figure 7B:
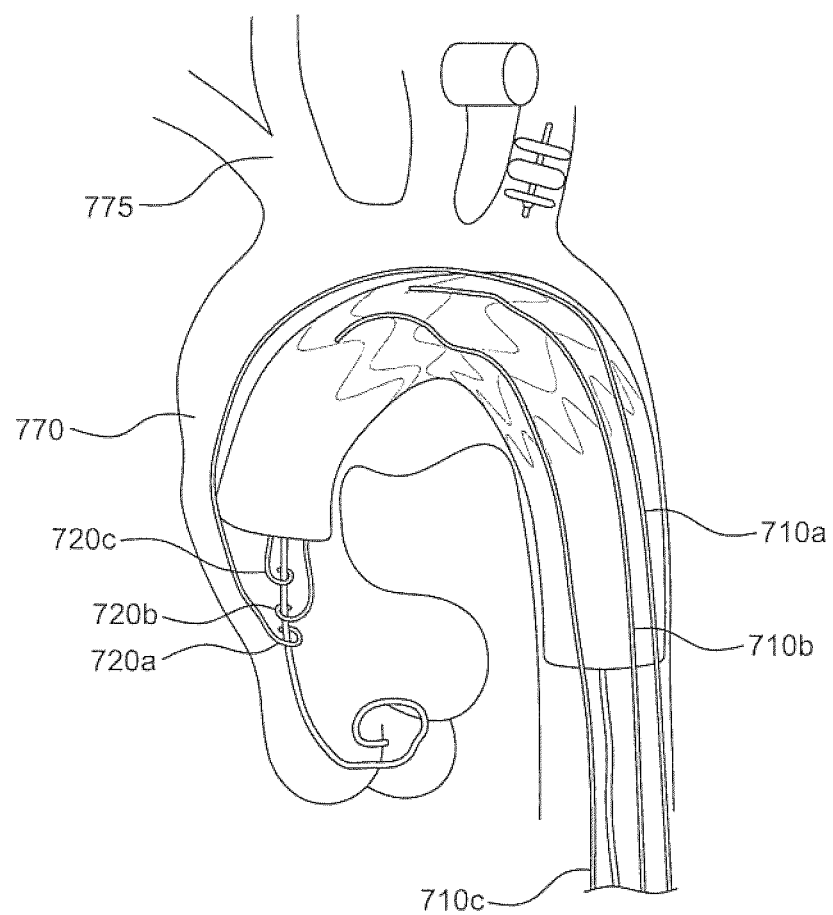
Figure 7C:
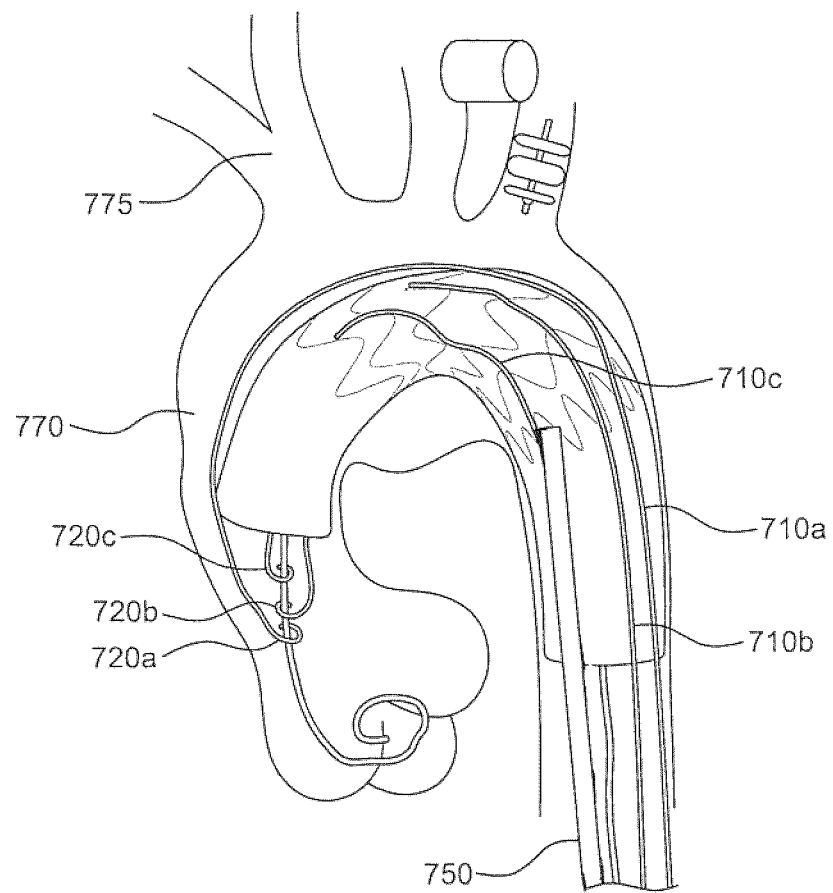
Figure 7D:
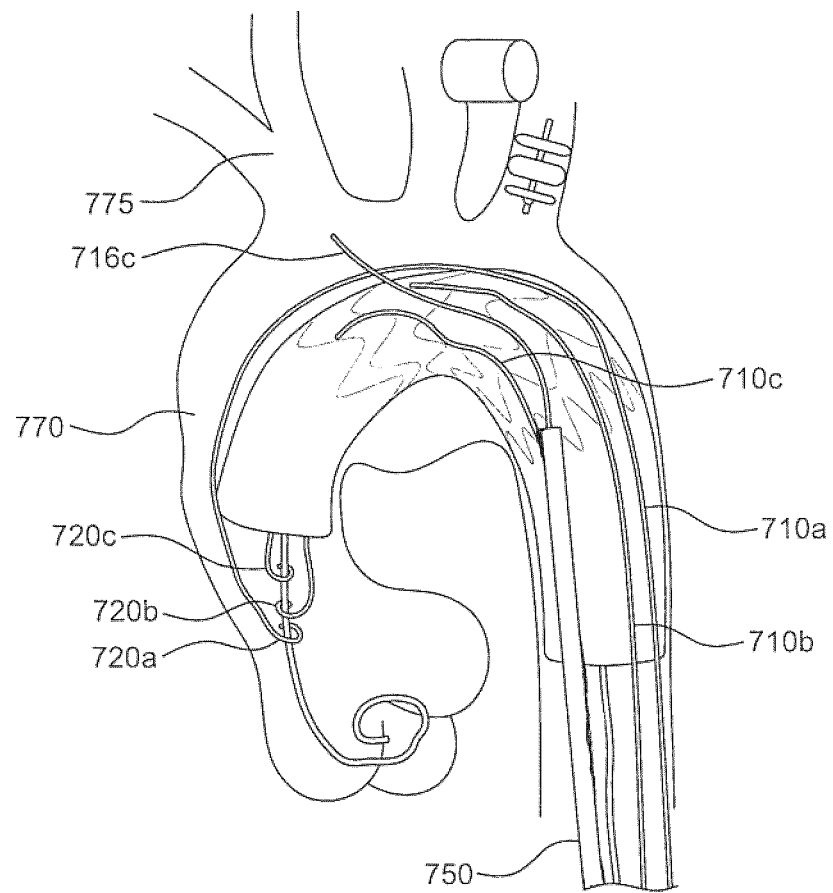
Figure 7E:
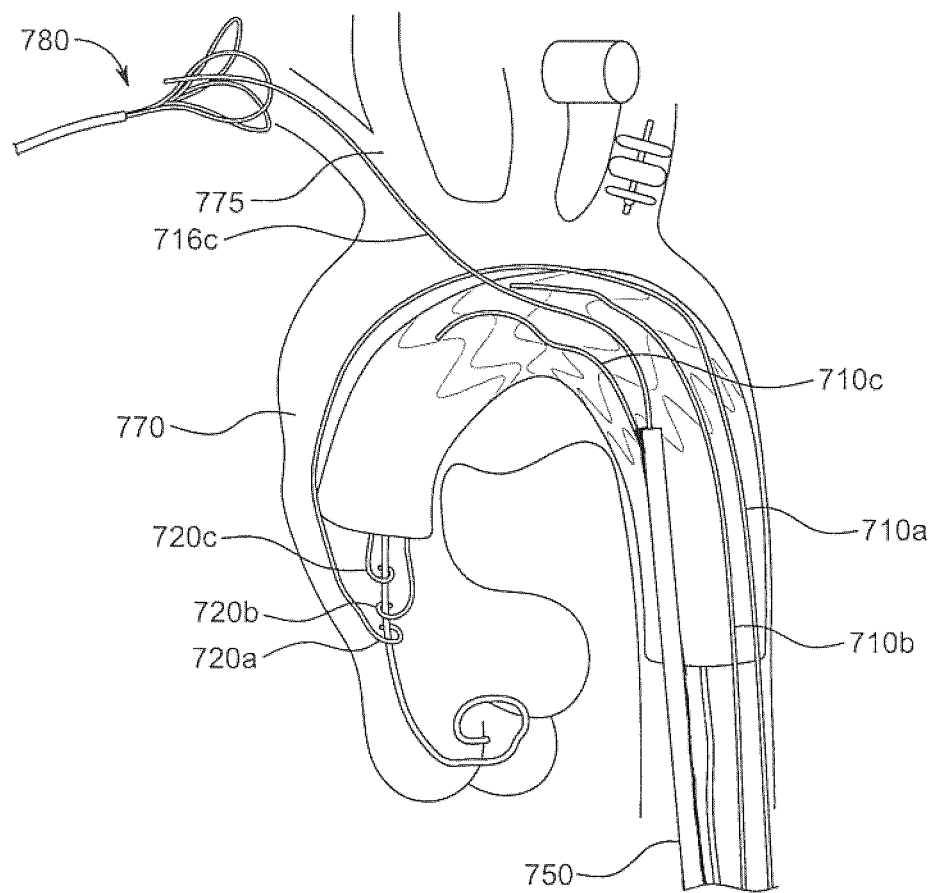
Figure 7F:
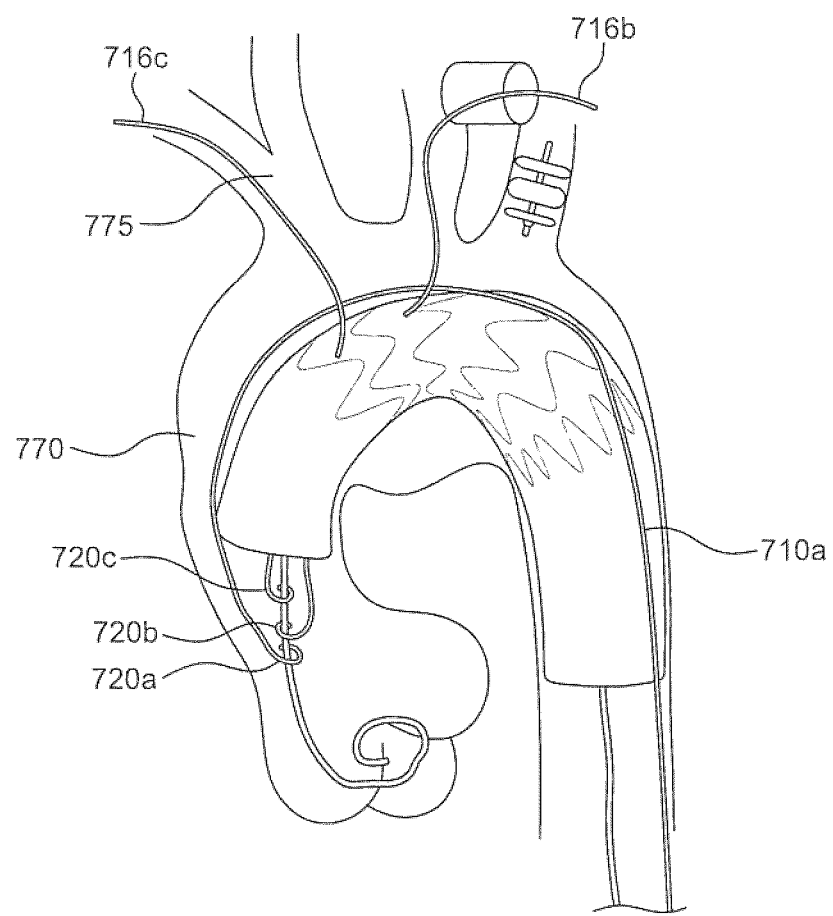

Turning to FIG. 7A, an aortic arch endograft 702 with two branches was pre-cannulated with three looped wires 710a, 710b, and 710c, and the respective first loops 720a, 720b, and 720c were anchored on the primary endovascular wire 730 ahead of the endograft. A carotid-subclavian bypass with embolization of the proximal left subclavian is shown, allowing the need for only two vessel revascularization in this example. One of the looped wires 710a keeps the other two 710b and 710c from slipping off the primary endovascular wire 730 when manipulation is occurring. This pre-cannulated endograft was advanced retrograde up to the aortic arch 770 from a first access point, aligned with a branch blood vessel 775 (see FIG. 7B), and deployed. A long sheath 750 was advanced over looped wire 710c from the first access point (see FIG. 7C), with the lagging end 716c of looped wire 710c extending out of the proximal end of the sheath 750 outside the body (not shown). This lagging end 716c of looped wire 710c was turned around and advanced back into the sheath 750 towards the deployed aortic arch endograft, and the lagging end 716c was positioned near the opening to the branch blood vessel 775 (see FIG. 7D). A loop was formed in the sheath. The other looped wire 710a, or the distal-most looped wire, was held taunt so that the looped wire does not slip off the primary endovascular wire 730, during this step. At this point, a snare 780 was introduced from a second access point downstream of the branch blood vessel 775 to snare the lagging end 716c of looped wire 710c, pulling the lagging end 716c out of the branch blood vessel out through the second access point (see FIG. 7E). The entire length of the looped wire 716c was pulled out from the second access point, such that it now extends from its anchor point on the primary endovascular wire 730, through a branch in the aortic arch endograft 702, through the branch blood vessel 775, and out the second access point (see FIG. 7F). The above steps are repeated for the other looped wires through other branch vessels. In this final configuration, a bridging stent was then introduced, for example, from the second access point to stent the branch blood vessel to the aortic arch endograft 702. When all the stenting was completed, the primary endovascular wire 730 is pulled out, releasing all the looped wires 710a, 710b, and 710c.

In this example, looped wire 710a anchors looped wires 710b and 710c, while they are being manipulated. In other examples, the anchoring looped wire is optional. In this example, looped wire 710a also enables pulling of the front end (nose cone) of the endograft to facilitate placement in the aortic arch, which is often angulated.

Although the embodiments have been described in detail, it should be understood that various changes, substitutions and alterations can be made herein. Moreover, the scope of the present application is not intended to be limited to the particular embodiments or examples described in the specification. As can be understood, the examples described above and illustrated are intended to be exemplary only. Moreover, the various features of the embodiments that have been described may be combined in various ways to produce numerous additional embodiments. It should also be understood that Figures are not presented to scale, and are instead shown as schematic illustrations.

The invention claimed is:

1. A pre-cannulated endograft system comprising:
   an endograft comprising a plurality of fenestrations or branches;
   a strand of material extending through a main body stent of the endograft, the strand of material having a thickness; and
   a plurality of pre-cannulation wires each comprising a looped wire comprising a flexible guidewire having a leading end and a lagging end, and a first loop located proximate to the leading end of the guidewire;
   wherein the first loops have an inner diameter that is larger than the thickness of the strand of material for threading the strand of material through the first loops and for sliding engagement of the first loops with the strand of material;
   wherein the strand of material is threaded through each of the first loops of the plurality of pre-cannulation wires in sliding engagement at a point ahead of the endograft, for anchoring the plurality of pre-cannulation wires to the strand of material, and
   wherein the plurality of pre-cannulation wires each extends through the main body of the graft and out through a respective one of the fenestrations or branches of the endograft.

2. The pre-cannulated endograft system of claim 1, wherein the endograft comprises at least the same number of pre-cannulation wires as there are fenestrations or branches and each of the plurality of fenestrations or branches has at least one pre-cannulation wire extending there through.

3. The pre-cannulated endograft system of claim 2, wherein the strand of material is threaded through the first loops of the pre-cannulation wires based on order of use.

4. The pre-cannulated endograft system of claim 1, wherein each of the plurality of pre-cannulation wires has a second loop located proximate to the lagging end of the guidewire.

5. The pre-cannulated endograft system of claim 1, wherein the endograft is a thoracoabdominal branch endoprosthesis or an iliac branch graft.

6. The pre-cannulated endograft system of claim 5, wherein the plurality of fenestrations or branches are configured as portals for receiving a plurality of bridging endografts that are deployable into target vessels.

7. The pre-cannulated endograft system of claim 1, wherein the strand of material is a suture or a thread.

8. The pre-cannulated endograft system of claim 1, wherein the first loops of the plurality of pre-cannulation wires each have an inner diameter of about 0.038 inches for threading a 0.035 inch strand of material through the first loops, or an inner diameter of about 0.040 inches for threading a 0.038 inch strand of material through the first loops.

9. The pre-cannulated endograft system of claim 1, wherein the guidewires are 0.018 inch in diameter and is a PTFE coated nitinol wire.

10. The pre-cannulated endograft system of claim 1, wherein each of the first loops is compressible into a compressed state for advancing the looped wires through a catheter, and wherein in the compressed state each of the first loops has a width of less than 0.035 inches for insertion through a 0.035 inch catheter.

11. The pre-cannulated endograft system of claim 1, wherein each of the leading ends of the plurality of pre-cannulation wires comprises a first floppy tip; and/or wherein each of the lagging ends of the plurality of pre-cannulation wires comprises a second floppy tip.

12. The pre-cannulated endograft system of claim 11, wherein the first and/or the second floppy tip comprises a tapered portion of the guidewire.

13. The pre-cannulated endograft system of claim 11, wherein the first and/or the second floppy tip is made by heating the leading and/or lagging end.

14. The pre-cannulated endograft system of claim 1, wherein the one or more of the first loops have a fastening means for opening and closing the loops.

15. The pre-cannulated endograft system of claim 1, wherein the one or more of the first loops are detachable.

16. The pre-cannulated endograft system of claim 1, comprising a second loop located proximate to the lagging end of each of the guidewires.

17. The pre-cannulated endograft system of claim 16, wherein the second loops are located at the lagging end of the guidewire.

18. The pre-cannulated endograft system claim 1, wherein at least one of the first loops is formed by looping the leading end of the guidewires.

19. A pre-cannulated endograft system comprising:
a deployment catheter;
an endograft mounted to the deployment catheter, the endograft having a plurality of fenestrations and/or a plurality of branches;
a plurality of pre-cannulation wires extending through the deployment catheter and through the plurality of fenestrations and/or the plurality of branches of the endograft when the endograft is in a compacted, delivery state, each of the plurality of pre-cannulation wires including a flexible guidewire having a leading end and a lagging end, and including a loop at the leading end; and
an anchor strand extending through the deployment catheter and threaded through at least one of the loops of the plurality of pre-cannulation wires at a point ahead of the endograft for anchoring the one or more pre-cannulation wires to the anchor strand.

20. The pre-cannulated endograft system of claim 19, wherein the plurality of fenestrations or branches are configured as portals for receiving a plurality of bridging endografts that are deployable into target vessels.

21. The pre-cannulated endograft system claim 19, wherein each of the loops is formed by looping the leading ends of the guidewires.

22. The pre-cannulated endograft system of claim 19, wherein each of the guidewires is a hybrid wire made of part endovascular wire and part suture material.

23. The pre-cannulated endograft system of claim 19, wherein the anchor strand includes a wire.

24. The pre-cannulated endograft system of claim 19, wherein the anchor strand includes a suture.

25. The pre-cannulated endograft system of claim 19, wherein each of the loops is attached to the flexible guidewires of the plurality of pre-cannulation wires.

* * * * *